United States Patent
Mauldin, Jr. et al.

(10) Patent No.: US 9,924,923 B2
(45) Date of Patent: Mar. 27, 2018

(54) ULTRASOUND IMAGING OF SPECULAR-REFLECTING TARGET

(71) Applicant: University of Virginia Patent Foundation, Charlottesville, VA (US)

(72) Inventors: F. William Mauldin, Jr., Charlottesville, VA (US); John A. Hossack, Charlottesville, VA (US); Kevin Owen, Crozet, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days.

(21) Appl. No.: 14/407,380

(22) PCT Filed: Jun. 13, 2013

(86) PCT No.: PCT/US2013/045576
§ 371 (c)(1),
(2) Date: Dec. 11, 2014

(87) PCT Pub. No.: WO2013/188625
PCT Pub. Date: Dec. 19, 2013

(65) Prior Publication Data
US 2015/0133788 A1    May 14, 2015

Related U.S. Application Data

(60) Provisional application No. 61/659,027, filed on Jun. 13, 2012.

(51) Int. Cl.
*A61B 8/00* (2006.01)
*A61B 8/08* (2006.01)
*A61B 8/14* (2006.01)

(52) U.S. Cl.
CPC .......... *A61B 8/4461* (2013.01); *A61B 8/0875* (2013.01); *A61B 8/145* (2013.01);
(Continued)

(58) Field of Classification Search
CPC ....... A61B 8/085; A61B 8/0891; A61B 8/463; A61B 8/469; A61B 8/523; A61B 8/00
See application file for complete search history.

(56) References Cited

U.S. PATENT DOCUMENTS 7,621,873 B2 *  11/2009  Owen .................... A61B 8/00
                                                      310/311
2006/0064010 A1   3/2006  Cannon, Jr. et al.
(Continued)

FOREIGN PATENT DOCUMENTS

CN    1042778 A    6/1990
CN    1968655 A    5/2007
(Continued)

OTHER PUBLICATIONS

"International Application Serial No. PCT/US2013/045576, International Search Report dated Sep. 19, 2013", 2 pgs.
"International Application Serial No. PCT/US2013/045576, Written Opinion dated Sep. 19, 2013", 7 pgs.
Hacihaliloglu, I., et al., "Bone surface localization in ultrasound using image phase-based features", Ultrasound Med Biol., 35(9), (Sep. 2009), 1475-87.
(Continued)

*Primary Examiner* — Joel Lamprecht
(74) *Attorney, Agent, or Firm* — Schwegman Lundberg & Woessner, P.A.

(57) ABSTRACT

Ultrasound apparatus or techniques can include obtaining reflected ultrasound echo information, which can be used to construct a two-dimensional or three-dimensional representation of an at least approximately specular reflected target, such as bone. In an example, echo information can be obtained from spatially-overlapping tissue regions, such as using one or more of an array of ultrasonic transducers, or mechanically-scanning one or more ultrasonic transducers. In an example, one or more of a deformable housing or a deformable coupling pad can be used, such as to couple ultrasonic energy between one or more transducers and a tissue region.

20 Claims, 16 Drawing Sheets

(52) U.S. Cl.
CPC .......... *A61B 8/4209* (2013.01); *A61B 8/4218* (2013.01); *A61B 8/4281* (2013.01); *A61B 8/4466* (2013.01); *A61B 8/4477* (2013.01); *A61B 8/4494* (2013.01); *A61B 8/461* (2013.01); *A61B 8/483* (2013.01); *A61B 8/523* (2013.01); *A61B 8/5207* (2013.01); *A61B 8/5253* (2013.01)

(56) References Cited

U.S. PATENT DOCUMENTS

| | | |
|---|---|---|
| 2006/0241430 A1 | 10/2006 | Lin |
| 2006/0264745 A1 | 11/2006 | Da Silva |
| 2007/0238998 A1 | 10/2007 | Nycz et al. |
| 2009/0024034 A1 | 1/2009 | Moreau-gobard et al. |
| 2011/0137175 A1 | 6/2011 | Hossack et al. |
| 2012/0029356 A1 | 2/2012 | Hossack et al. |
| 2012/0157834 A1 | 6/2012 | Lazebnik |
| 2013/0172743 A1 | 7/2013 | Brewer et al. |
| 2014/0350390 A1 | 11/2014 | Kudavelly et al. |

FOREIGN PATENT DOCUMENTS

| | | |
|---|---|---|
| CN | 102068275 A | 5/2011 |
| CN | 104661600 A | 5/2015 |
| DE | 102010047155 A1 | 5/2011 |
| JP | 2007313114 A | 12/2007 |
| WO | WO-0216963 A2 | 2/2002 |
| WO | WO-2008071454 A2 | 6/2008 |
| WO | WO-2009020617 A1 | 2/2009 |
| WO | WO-2011094585 A1 | 8/2011 |
| WO | WO-2013188625 A1 | 12/2013 |
| WO | WO-2015025183 A1 | 2/2015 |

OTHER PUBLICATIONS

Mauldin, F. W, et al., "The effects of transducer geometry on artifacts common to diagnostic bone imaging with conventional medical ultrasound", IEEE Transactions on Ultrasonics, Ferroelectrics and Frequency Control, 59(6), (2012), 1101-1114.

Walker, W. F, "C- and D-weighted ultrasonic imaging using the translating apertures algorithm", IEEE Transactions on Ultrasonics, Ferroelectrics and Frequency Control, 48(2), (2001), 452-461.

"Chinese Application Serial No. 201380043131.1, Office Action dated Feb. 16, 2016", W/ English Translation, 18 pgs.

"Chinese Application Serial No. 201380043131.1, Office Action dated Oct. 8, 2016", with English Translation, 17 pgs.

"European Application Serial No. 13803513.4, Extended European Search Report dated Dec. 22, 2015", (7 pgs).

"International Application Serial No. PCT/US2013/045576, International Preliminary Report on Patentability dated Dec. 24, 2014", 9 pgs.

"Chinese Application Serial No. 201380043131.1, Response filed Dec. 23, 2016 to Office Action dated Oct. 8, 2016", W/ English Claims, 10 pgs.

"Chinese Application Serial No. 201380043131.1, Office Action dated Mar. 31, 2017", w/ English Translation, 17 pgs.

"Chinese Application Serial No. 201380043131.1, Office Action dated Aug. 30, 2017", w/English Translation, 20 pgs.

"Chinese Application Serial No. 201380043131.1, Response filed Aug. 15, 2017 to Office Action dated Mar. 31, 2017", W/English Claims, 9 pgs.

"Chinese Application Serial No. 201380043131.1, Response filed Nov. 8, 2017 to Office Action dated Aug. 30, 2017", W/English Claims, 10 pgs.

\* cited by examiner

ULTRASOUND IMAGING OF SPECULAR-REFLECTING TARGET

CLAIM OF PRIORITY

This application is a U.S. National Stage Filing under 35 U.S.C. 371 from International Patent Application Serial No. PCT/US2013/045576, filed on Jun. 13, 2013, and published on Dec. 19, 2013 as WO 2013/188625, which claims the benefit of priority of U.S. Provisional Patent Application Ser. No. 61/659,027, filed on Jun. 13, 2012, the benefit of priority of each of which is claimed hereby, and each of which is incorporated by reference herein in its entirety.

BACKGROUND

In the United States, overcrowding of Emergency Departments (EDs) occurs at least once per week in 90% of hospitals. ED overcrowding is correlated with poor health outcomes, resulting in a higher mortality rate or longer recovery time, such as due to a lack of timeliness and an inability to administer treatment. There are many causes of ED overcrowding, predominantly including high demand for radiology services. Such radiology services include 39 million X-rays provided for EDs each year. Many X-rays are acquired for patients with time-critical conditions (e.g., trauma, head injury, or stroke), and about 19 million are acquired for patients with suspected bone fractures.

For example, X-rays for bone fractures include 4 million patients per year who receive 2 X-ray sessions each, with 60% of these patients receiving two sets of X-rays per session (estimated using a percentage of displaced fractures). X-rays are also obtained for 3.2 million of the 5 million ED sprain patients per year (estimated using a statistic that 64% of ED sprains receive X-rays). Acquiring an X-ray for a patient in the ED is resource intensive and time consuming, and generally can involve the following: arrangement of time on the X-ray machine, transport of the patient to the X-ray machine, acquisition of the X-ray image, transport of the patient and the image results back to the ED, obtaining a disposition from a radiologist, and communication of the disposition to the ED or an orthopedic physician. For example, each ED-ordered X-ray consumes >30 minutes with an additional >30 minutes to acquire a radiologist disposition. Delay can also be compounded by the radiology backlog.

OVERVIEW

In one approach, generally-available two-dimensional (2D) ultrasound apparatus can be used instead of X-ray such as for fracture detection and monitoring of treatment (e.g., fracture reduction). Use of such generally-available 2D ultrasound for ED fracture detection generally results in faster diagnosis and treatment times at less cost. However, sensitivity or specificity for detection of bone fractures using such generally-available 2D ultrasound can be inferior to X-ray. For example, it has been previously determined that 2D ultrasound-based diagnosis of ankle fractures can result in 90.9% sensitivity and 90.9% specificity. Several weaknesses of the 2D approach contribute to its inferior fracture detection properties, for example: bone image quality can be poor; imaging field of view can be limited (e.g., a 4 centimeter (cm) by 1 cm footprint such as with a 5-6 cm imaging depth); and image acquisition and interpretation of imaging results can generally involve significant user skill.

In contrast, the present inventors have recognized that various ultrasound techniques and apparatus can be used for reliable determination of bone fractures, or generally for imaging one or more imaging targets, such as one or more specular-reflecting targets within tissue. In an example, an ultrasound imaging technique can include Specular surface Reconstruction using Multi-angle Interrogation (SRMI), such as using an array of ultrasonic transducers (e.g., an array of piston transducers).

In an example, an ultrasound apparatus can include one or more processor circuits coupled to a display, and a conformable imaging transducer assembly that can be positioned nearby a tissue region to be imaged, such as conformed to a profile of the tissue region (e.g., a leg, an arm, an ankle, an elbow, or one or more other sites). For example, such an array can include the processor circuit and display in a self-contained housing, or the ultrasonic transducer assembly can be coupled to a separate apparatus such as a cart including the display, one or more user inputs, or other circuitry. Such apparatus can include a processor-readable medium comprising instructions that when performed by one or more processor circuits, cause the one or more processor circuits to construct a representation of an at least approximately specular-reflecting target.

Generally, ultrasound apparatus or techniques described herein can include obtaining reflected ultrasound echo information, which can be used to construct a two-dimensional or three-dimensional representation of an at least approximately specular reflected target, such as bone. In an example, echo information can be obtained from spatially-overlapping tissue regions, such as using one or more of an array of ultrasonic transducers, or mechanically-scanning one or more ultrasonic transducers. In an example, one or more of a deformable housing or a deformable coupling pad can be used, such as to couple ultrasonic energy between one or more transducers and a tissue region.

This overview is intended to provide an overview of subject matter of the present patent application. It is not intended to provide an exclusive or exhaustive explanation of the invention. The detailed description is included to provide further information about the present patent application.

Figure 1:
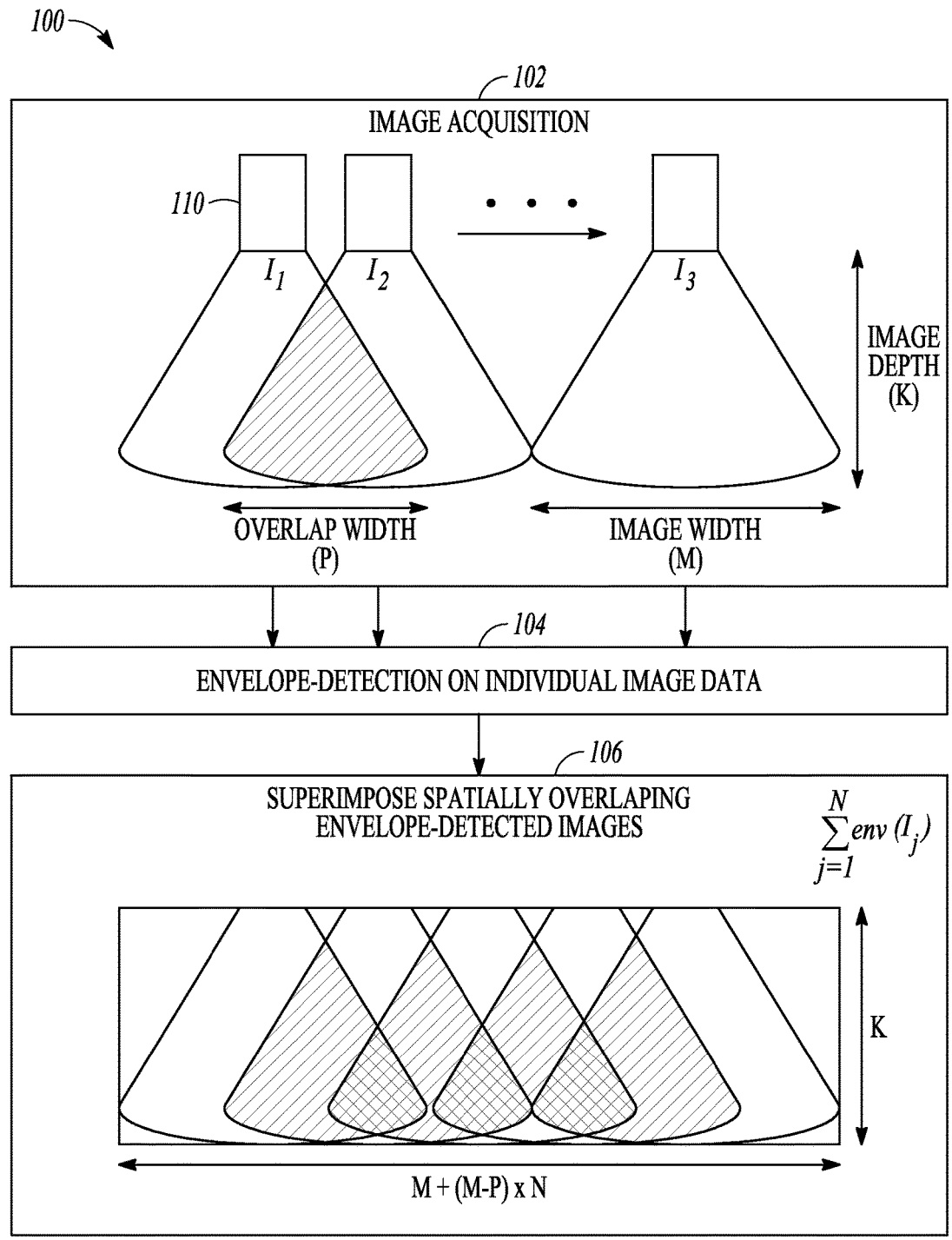
FIG. 1 illustrates generally of an example of at least a portion of an ultrasonic apparatus and a corresponding technique.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

FIG. 1 illustrates generally of an example 100 of at least a portion of an ultrasonic apparatus and a corresponding technique. At 102, one or more transducers can be positioned to obtain echo information corresponding to sector scans with overlapping imaging planes. The overlapping image planes can be acquired including respective ranges of imaging angles.

For example, at 102, respective imaging planes (e.g., a sector scan plane) can be represented as $I_1$, $I_2$, and $I_3$, (or $I_N$, where $N$ represents the Nth image scan plane). Respective sector planes can be acquired, such as including an overlap width, which can be represented by P, and a plane image width, which can be represented by M, and an image depth, which can be represented by K.

At 104, such echo information can be envelope-detected and at 106 a Specular surface Reconstruction using Multi-angle Interrogation (SRMI) technique can be used to form a representation at least in part by superimposing imaging information corresponding to the overlapping imaging planes. For example, spatially-overlapping envelope-detected images can be superimposed on each other as shown in FIG. 1.

A representation of a specular surface, such as bone within tissue, can be formed using the SRMI technique shown in FIG. 1 and discussed below in relation to the example of FIG. 15. For example, an apparatus can include an array of ultrasonic transducers, such as aligned along a linear path (e.g., a piston array such as discussed in other examples below). The SRMI technique can benefit from a large spacing, with respect to an acoustic wavelength, between the transmit apertures (e.g., such apertures as defined by the transducers). Such large spacing enables interrogation of targets over a wide range of angles. As a result, sensitivity to specular targets and compounding of diffusive scattering targets are enhanced in the resulting reconstructed image or representation. Such factors can provide a representation having enhanced overall image contrast, and in particular, improved bone-to-tissue image contrast, as compared to generally-available 2D ultrasound apparatus and techniques.

SRMI can be performed using transducers having transmit apertures that are spaced widely apart. In contrast, transmit aperture spacing is generally smaller for generally-available linear array transducers, such as due to limitations in the number of transducer channels that can be supported. In an illustrative example, more than about 560 elements or channels in a sampled linear array with ½ wavelength pitch would be required to cover the same overall aperture size (and angular interrogation span) as can be covered with six piston transducers, such as operating at a 5 megahertz (MHz) center frequency, such as can include about 1 cm diameter piston transducers spaced about 1.5 cm apart.

In an example, single-element transducers can be located greater than about a wavelength apart, or many independently operating sampled-array transducers (e.g., many linear array transducers) can be arranged so that a between-element spacing is less than or equal to about a ½ wavelength and a between-aperture spacing is about one wavelength or larger. In another example, a single-element or sample-array transducer can be mechanically scanned using a motor to obtain information from more than one location such as to provide echo information similar to the information that can provided by a larger array of transducers.

In an example, SRMI can be performed using information obtained using a single piston transducer attached to a motor. For example, the motor can translate the piston transducer to locations along a specified path (e.g., a linear path). At various locations along the path, an imaging scan can be performed. Such locations can be specified so that imaging scans acquired at different locations would include overlapping scan regions. Other techniques or apparatus for position the transducer can also be used. For example, a sector scan can be performed such as by mechanically "wobbling" the piston transducer with a motor (e.g., rotating the piston transducer back-and-forth through a specified range of angles). SRMI can be performed by superimposing the echo information obtained from transducers at different locations prior to envelope-detection, such as echo information obtained from overlapping scan regions.

In an example, the ultrasonic transducer array can include several sampled array transducers. Sector scan imaging can be performed by electronic transmit delays or dynamic receive focusing at a compilation of respective scan angles. In an example including single-element transducers, such transducer geometries need not be circular. For example, such transducer geometries can include approximately equal aperture dimensions (e.g. square, hexagonal) and can be used in place of or in addition to circular (e.g., piston) transducers.

Figure 2A:
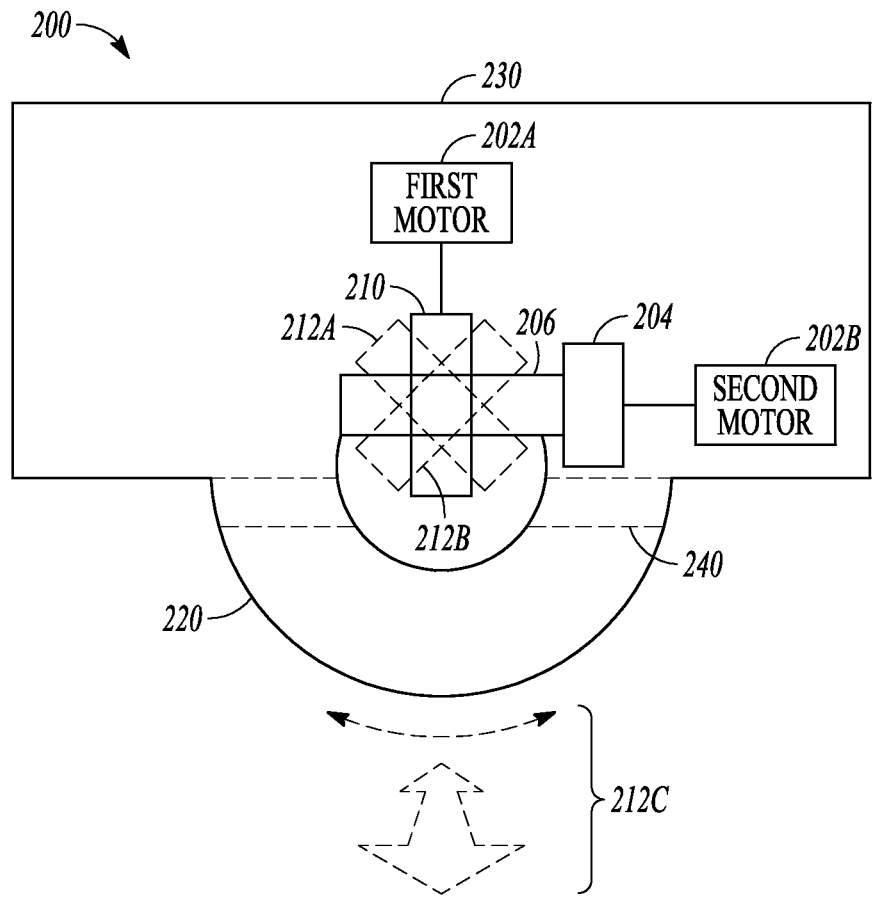
FIG. 2A illustrates generally an example of at least a portion of an ultrasonic apparatus, including one or more transducers that can be mechanically scanned such as to obtain echo information from a three-dimensional volume.

FIG. 2A illustrates generally an example of at least a portion of an ultrasonic apparatus 200, including one or more ultrasonic transducers that can be mechanically scanned such as to obtain echo information from a three-dimensional volume. For example, a transducer 210 can be mechanically positioned using a first motor 202A or a second motor 202B, such as coupled to the transducer 210 using a mechanical coupling 206. A sprocket assembly 204 can be used, such as to transfer the rotational motion of the second motor 202B into linear motion to translate the transducer 210. The first motor 202A can be coupled to the transducer 210, such as to wobble or rotate the transducer 210 in first direction 212A or a second direction 212B. In this manner, the transducer can be mechanically positioned translationally and rotationally in the directions as shown at 212C.

The apparatus 200 can include a housing, such as to provide a hand-held transducer assembly. A coupling pad 220 can be included, such as a rigid or deformable coupling pad. A fluid or gel 240 can be included in a cavity region within the coupling pad 220 or housing 230, such as to couple acoustic energy from the transducer 210 to a tissue region.

Figure 2B:
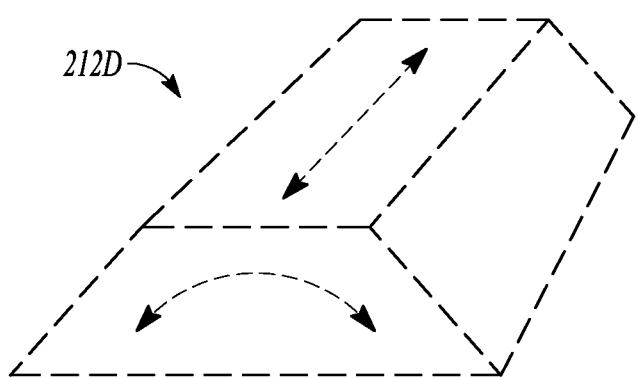
FIG. 2B illustrates generally an example of a shape of a three-dimensional volume, such as can be acquired using the apparatus shown in FIG. 2A.

FIG. 2B illustrates generally an example of a shape of a three-dimensional volume 212D, such as can be acquired using the apparatus shown in FIG. 2A. The scan volume 212D can be obtained using respective motors to rotate or translate one or more transducers, such as shown in FIG. 2A. In an example, the SRMI techniques discussed above and below (e.g., in FIGS. 1 and 15) can include using a single sparsely-sampled transducer array, such as including one or more sub-arrays spaced at greater than or equal to one wavelength apart, such as including an element spacing less than or equal to one wavelength in a respective sub-array.

Figure 3:
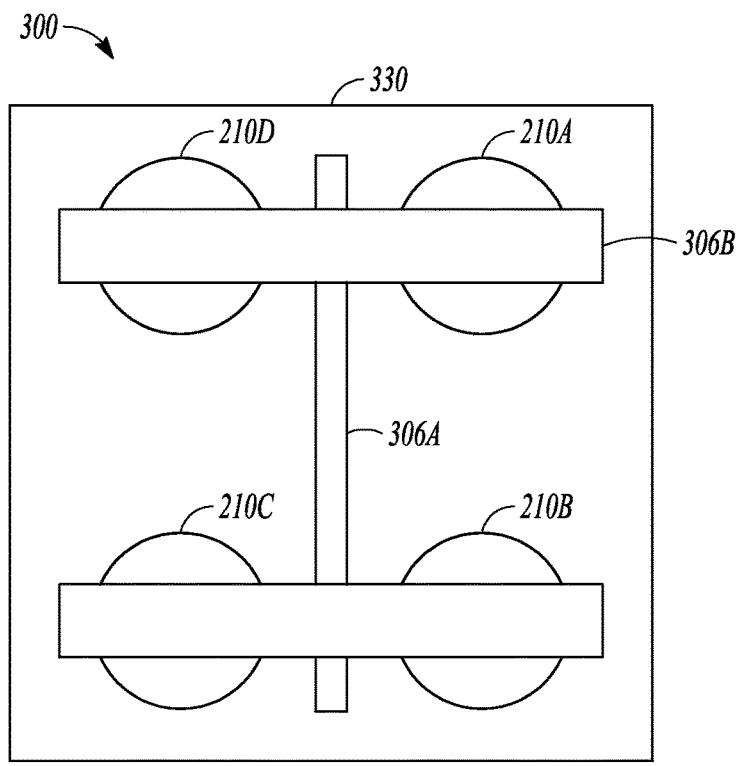
FIG. 3 illustrates generally an example of at least a portion of an ultrasonic apparatus, such as can include an array of ultrasonic transducers.

FIG. 3 illustrates generally an example of at least a portion of an ultrasonic apparatus 300, such as can include an array of ultrasonic transducers, 210A through 210D. The ultrasonic transducers can be anchored, such as using one or more of a first mechanical coupling 306A (e.g., a rail, a pin, or other structure), such as coupled to a second mechanical coupling 306B. The ultrasonic transducers can be anchored in a manner to provide spatially-overlapping acoustic beams, such as including an angled mounting shown in the example of FIG. 4A.

Figure 4A:
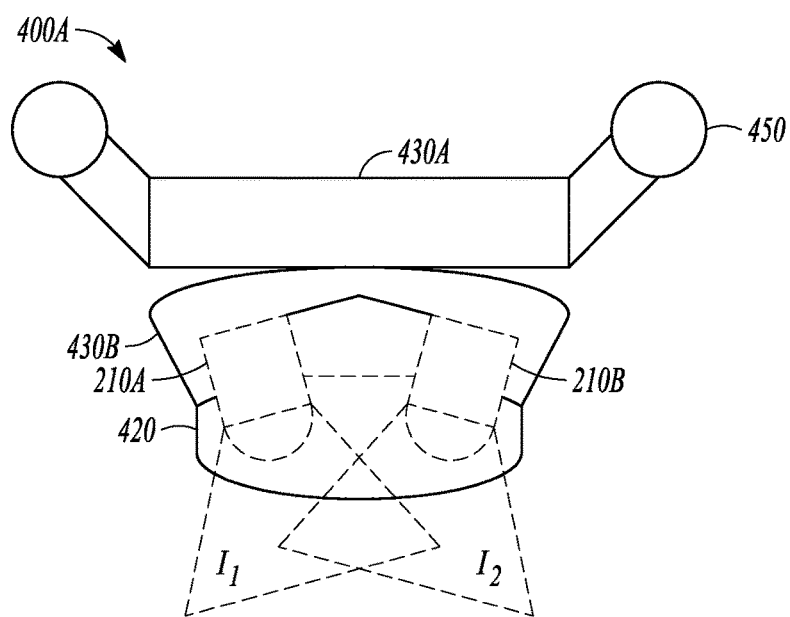
FIG. 4A illustrates generally an example of at least a portion of a hand-held ultrasonic apparatus, such as can include two or more ultrasonic transducers configured to obtained echo information from regions including volumes having overlapping acoustic beams.
Figure 4B:
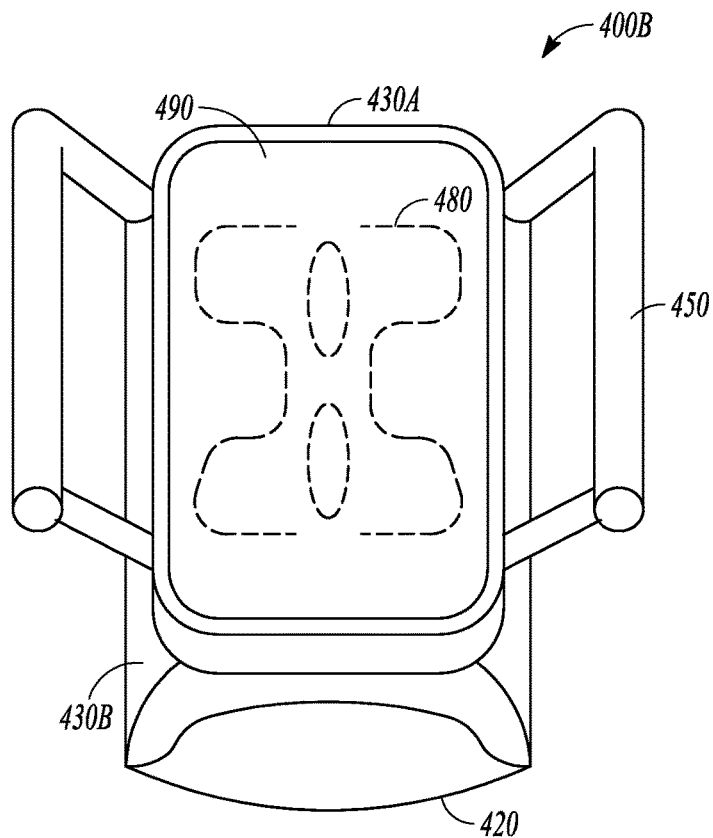
FIG. 4B illustrates generally an example of at least a portion of a hand-held ultrasonic apparatus, such as similar to the example of FIG. 4A.

FIG. 4A illustrates generally an example of at least a portion of a hand-held ultrasonic apparatus 400A, such as can include two or more ultrasonic transducers 210A and 210B, configured to obtained echo information from respective regions I1, I2, including volumes having overlapping acoustic beams. FIG. 4B illustrates generally an example of at least a portion of a hand-held ultrasonic apparatus 400B, such as similar to the example of FIG. 4A, such as can include a display 490, to provide a representation of an imaging target 480 (e.g., a specular-reflecting target such as bone). In FIGS. 4A and 4B, a first portion 430A of a housing can include the display, acquisition or processor circuits including transducer drivers or signal conditioning circuits, and one or more handles or grips 450 or other implements to facilitate user manipulation of the apparatus 400B, and a second portion 430B of the housing can include one or more ultrasonic transducers and a rigid or deformable coupling pad 420.

The apparatus of FIG. 3 or FIG. 4A or 4B can be freely translated or otherwise freely manipulated by a user to construct a representation of a specular-reflecting target. The "bent" or angled mounting of the transducers as shown in FIG. 4B can yield highly overlapping acoustic beams (dotted), such as to reduce or eliminate blind spots, and to obtain echo information from multiple directions.

Figure 6:
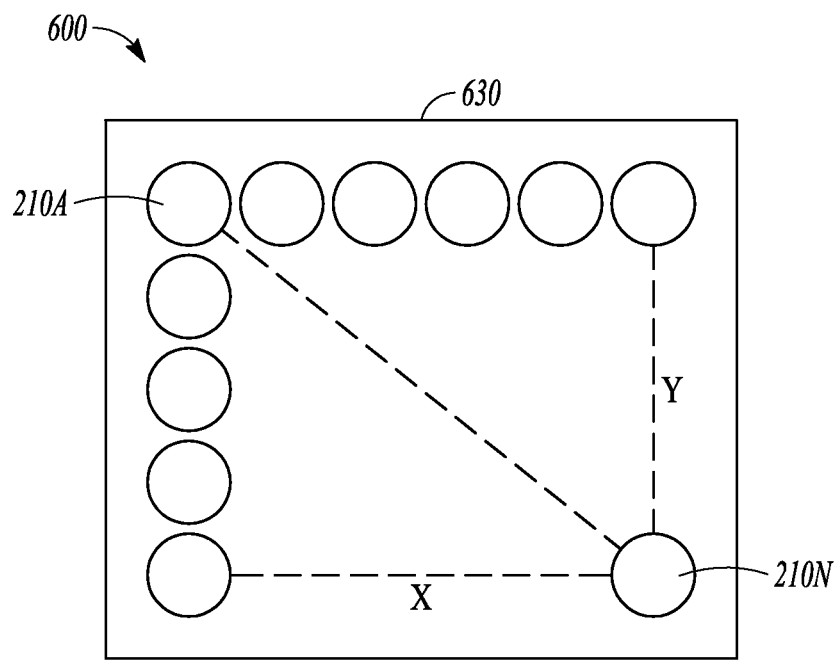
FIG. 6 illustrates generally an example of a two-dimensional array of ultrasonic transducers.

Apparatus, such as included in one or more of the examples shown and discussed above or below can include three-dimensional (3D) imaging capability. For example, such apparatus can include one or more transducers configured to obtain echo information for use in construction of a 3D representation of a target, such as can include one or more specular-reflecting targets. One or more transducers can be used to acquire sector scans such as from specified locations in 3D space, such as can include locations along a curved mounting frame or arranged in a 2D grid as shown in the example of FIG. 4A or FIG. 6. An image shown on the display 490, such as shown in FIG. 4C, can be spatially registered to underlying anatomy, to provide the illusion of a "window" through the skin.

Figure 5:
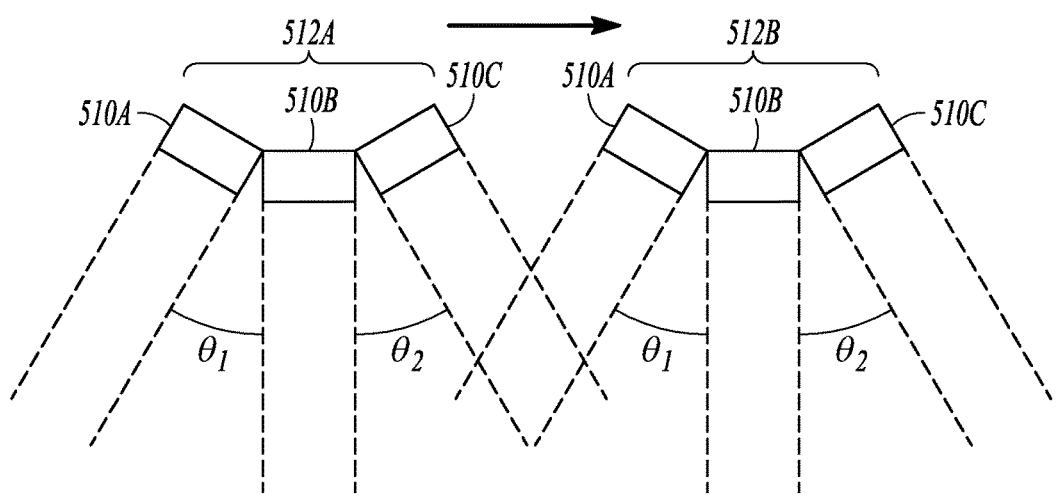
FIG. 5 illustrates generally an example of transducer arrangement that can be directed at different relative imaging angles, such as to acquire overlapping volumes.

FIG. 5 illustrates generally an example of a transducer arrangement 500 that can be directed at different relative imaging angles, such as to acquire overlapping volumes. The example of FIG. 5 can include one or more single-element or sampled-array transducers, such as directed at different relative imaging angles. Such a configuration can be used to acquire overlapping image planes or volumes, such as for use with an SRMI image reconstruction technique. For example, at a first location 512A, a first ultrasonic transducer 510A can obtain echo information. At the first location 512A, a second ultrasonic transducer 510B can obtain information at a fixed angle $\theta_1$ with respect to the first ultrasonic transducer 510A, and a third ultrasonic transducer 510C can obtain information at a fixed angle $\theta_2$ with respect to the second ultrasonic transducer 510B.

Alternatively, a single ultrasonic transducer can be rotated or "wobbled" through the range of angles shown, rather than using three separate ultrasonic transducers 510A through 510C arranged at fixed angles. The one or more ultrasonic transducers can then be repositioned to a second location 512B, and a similar range of angles can be scanned, either using fixed transducers, or by rotating a single transducer, such as to obtain echo information corresponding to an scan plane or volume that at least partially overlaps with the region scanned at the first location 512A.

FIG. 6 illustrates generally an example 600 of a two-dimensional array of ultrasonic transducers, such as can be arranged in a two-dimensional (2D) grid, and such as enclosed within a housing 630. The array can include respective transducers such as transducer 210A through transducer 210N (e.g., a piston-shaped transducer), and the array can extend along a first axis, x, and a second axis, y. Respective transducers in the array can be translated or rotated (e.g., wobbled) using one or more motors, to create overlapping sector scan planes or volumes for image reconstructions, such as for use with an SRMI technique.

Figure 7:
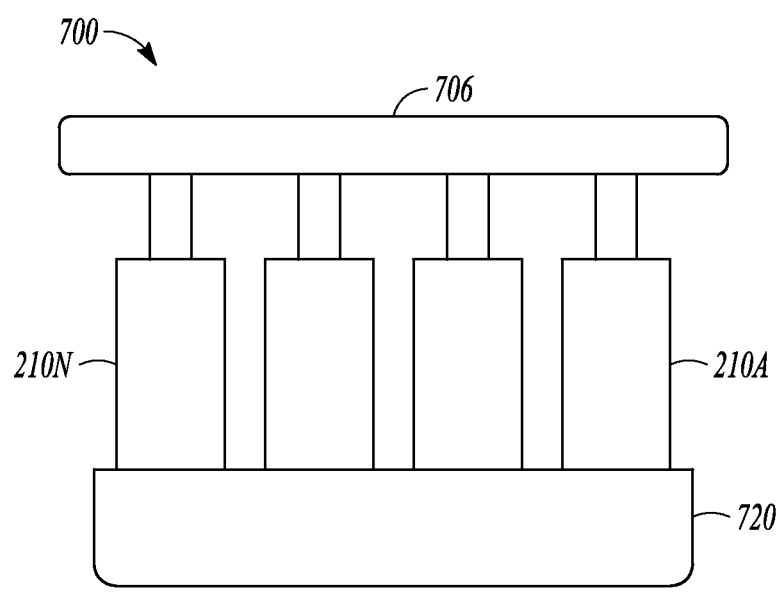
FIG. 7 illustrates generally an example of an array of ultrasonic transducer elements, such as can be acoustically coupled to a tissue region using a coupling pad.
Figure 8A:
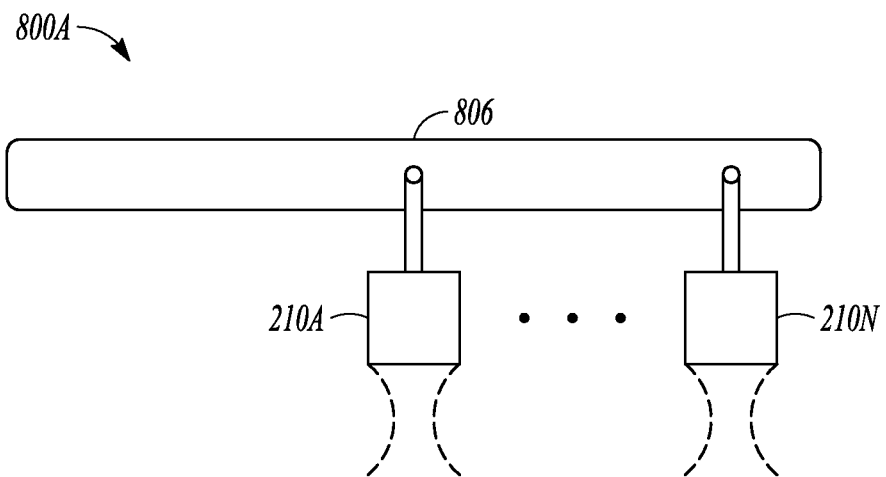
FIGS. 8A and 8B illustrate generally an illustrative example of positioning ultrasonic transducers in manner to rotate the transducers, using a mechanical coupling.
Figure 8B:
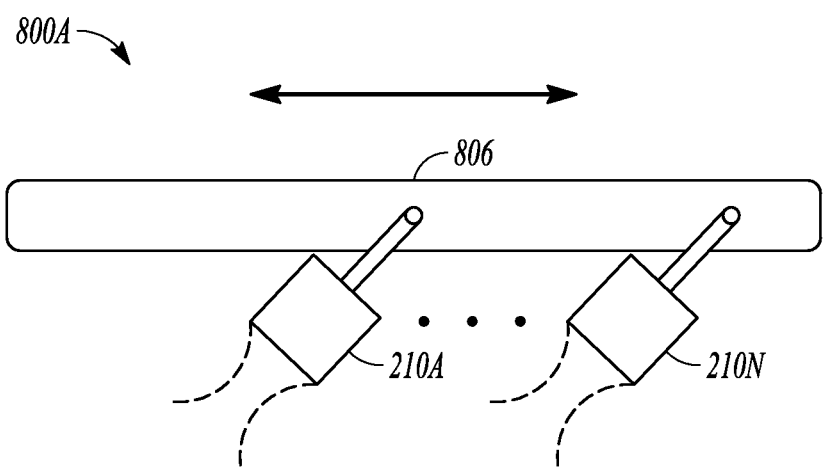

FIG. 7 illustrates generally an example of an array of ultrasonic transducer elements, such as can be acoustically coupled to a tissue region using a coupling pad 720. For example, respective transducers 210A through 210N can be respectively coupled to a mechanical coupling 706 for actuation via a motor or linear actuator, such as shown in other examples such as FIGS. 8A and 8B. FIGS. 8A and 8B illustrate generally an illustrative example of positioning ultrasonic transducers 210A through 210N in manner to rotate the transducers 210A through 210N, such as using a mechanical coupling 806 (e.g., a rail, rod, arm or other assembly). For example, in a first position 800A, respective transducers 210A through 210N can be oriented in a first direction, and in a second position 800B of the mechanical coupling 806, the transducers 210A through 210N can pivot to be oriented in a second direction. For example, as the mechanical coupling 806 oscillates, the transducers 210A through 210N can pivot bi-directionally around the neutral position shown in FIG. 8A. Respective transducers 210A through 210N can include a pin or hinged arrangement, such as including one or more dampers or springs.

Figure 9A:
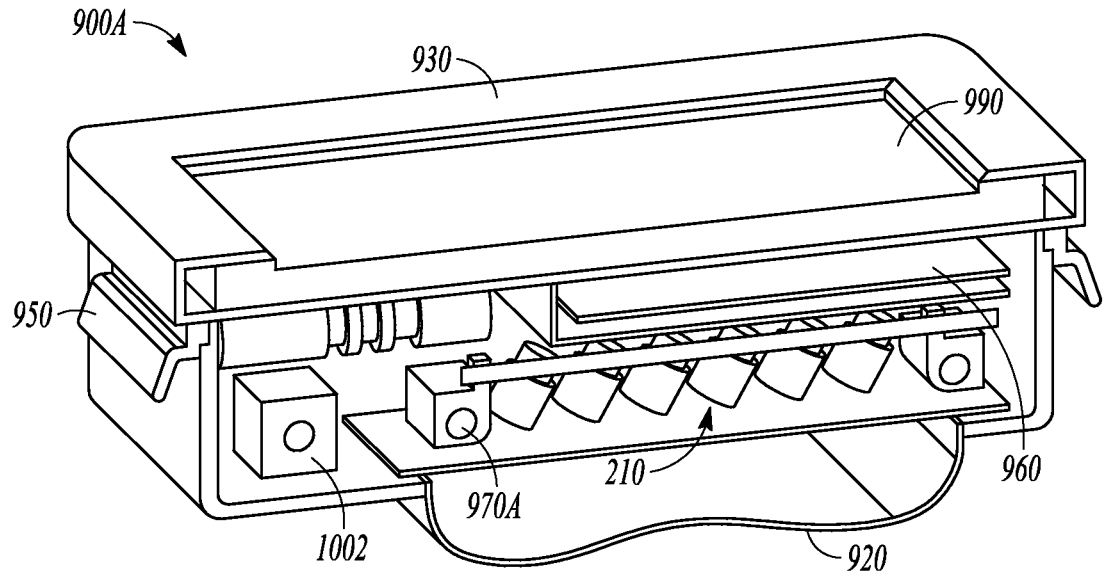
FIGS. 9A through 9C illustrate generally portions of an illustrative example of a hand-held ultrasonic apparatus, such as including an ultrasonic transducer array, a mechanical positioner, and a display.
Figure 9B:
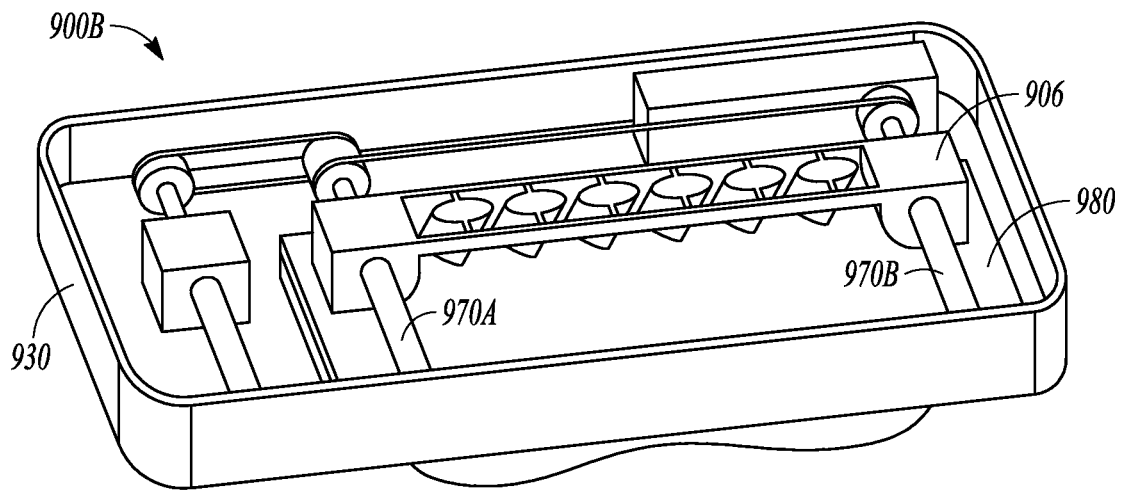
Figure 9C:
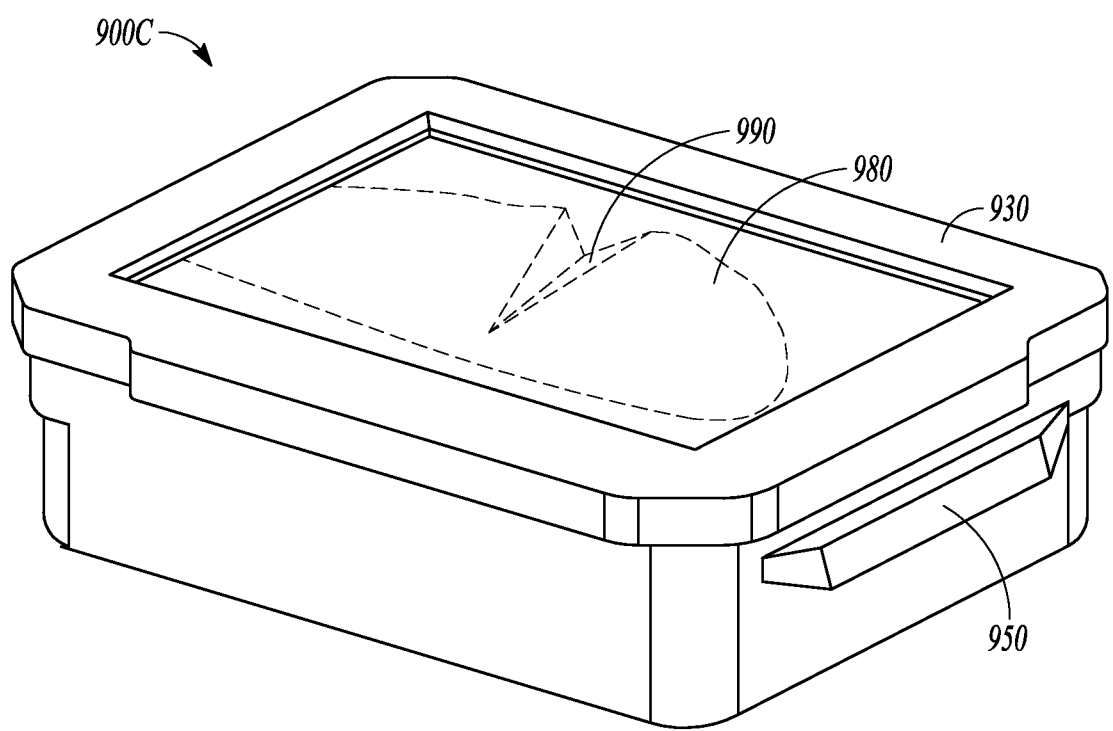

FIGS. 9A through 9C illustrate generally portions of an illustrative example of a hand-held ultrasonic apparatus, such as including an ultrasonic transducer array comprising respective ultrasonic transducer elements (e.g., a piston-type transducer element 210), a mechanical positioner, and a display 990. Respective single element transducers can be manipulated with a mechanical positioner including one or more motors or actuators to drive one or more rails, belts, chains, pulleys, sprockets, lead screws, or other mechanical couplings, for example, to perform a sector scan such as to obtain a set of sector scans from different single elements that include overlapping sector regions. Such overlapping sector scan regions can provide ultrasound echo information obtained from multiple angles, as reflected or otherwise scattered by a target region.

In the example of FIGS. 9A through 9C, transducers can be one or more of rotated with a first motor 1002 to provide a sector scan in one dimension (e.g., along a direction as shown at 980), or translated (e.g., linearly) with the first motor 1002 or another motor. For example, a first lead screw and a second lead screw can position a carriage 906 to translate the transducer array. In this manner, echo information corresponding to a 3D volume can be obtained. Such single element transducers can include piston transducers, such as including a focusing lens or focusing geometry. Such relatively large piston transducers can be advantageous for imaging specular reflecting targets (e.g., bone), such as because off-axis artifacts from grating lobes are suppressed. Also, a signal-to-noise ratio (SNR) can be enhanced when imaging deep bone targets such as due to a large available transducer area.

The present inventors have also recognized, among other things, that such piston transducers could be made conformable to an imaging surface, such as using a coupling pad 920 (e.g., a deformable coupling bladder), such as shown in the examples of FIGS. 9A through 9C. Such a conformable or deformable coupling bladder can be included as a portion of the transducer apparatus. For example, an interior space defined by such a bladder can share a coupling fluid with other internal portions of the apparatus. Such a coupling bladder can be a separate detachable unit, such as defining a coupling fluid reservoir separate from other coupling fluid. In an example, the coupling bladder can be coupled to a portion of a transducer element or array, such as between the array and skin of a patient, such as using ultrasound gel or one or more other acoustic coupling materials.

The examples of FIGS. 9A through 9C illustrate generally an illustrative examples 900A through 900C of a user-manipulated ultrasound apparatus that can include a handle or grip 950, a housing 930, a display 990, and a processor circuit assembly 960. The processor circuit assembly can include one or more circuits configured or programmed to obtained echo information, process echo information, construct an image, or communicate with other devices or circuits, for example. In the examples of FIGS. 9A through 9C, one or more of the transducer assembly or coupling pad can be commonly shared with a housing 930 including other portions of the apparatus such as a processor circuit assembly 960 or display 990 as shown, or, in other examples, the transducer assembly can be separate from the other apparatus, such as coupled via a wireless or wired coupling, such as shown in the examples of FIGS. 12A and 12B, or FIGS. 17A and 17B.

In FIG. 9C, a 3D representation of an imaging target 980 is shown. According to various examples, a housing 930 and display 990 as shown in FIG. 9C can include a 2D sampled array, a mechanically scanned 2D array, mechanically scanned single elements, or one or more other configurations of ultrasonic transducer elements. For example, a mechanically-scanned linear array is shown in the examples of FIGS. 9A and 9B. The present inventors recognize that image display methods can include ultrasound image processing and display techniques such as described generally in FIG. 1 or FIG. 15, to obtain the reconstruction shown in the illustrative example of FIG. 9C, such as constructed using an SRMI technique. Such imaging information can be log compressed for display, for example.

Figure 10A:
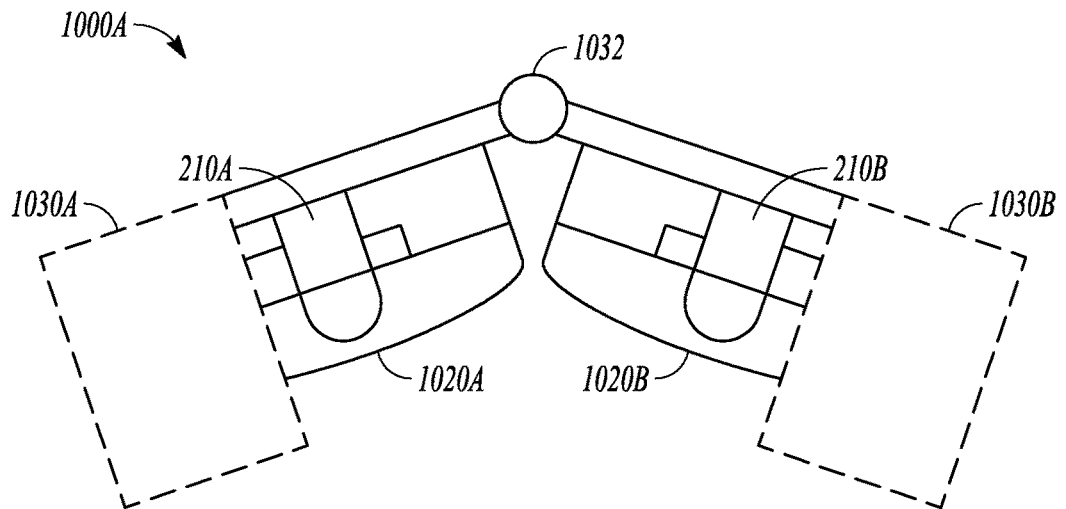
FIGS. 10A and 10B illustrate generally portions of other illustrative examples of a hand-held ultrasonic transducer assembly, such as including a mechanical coupling between respective portions of a housing.
Figure 10B:
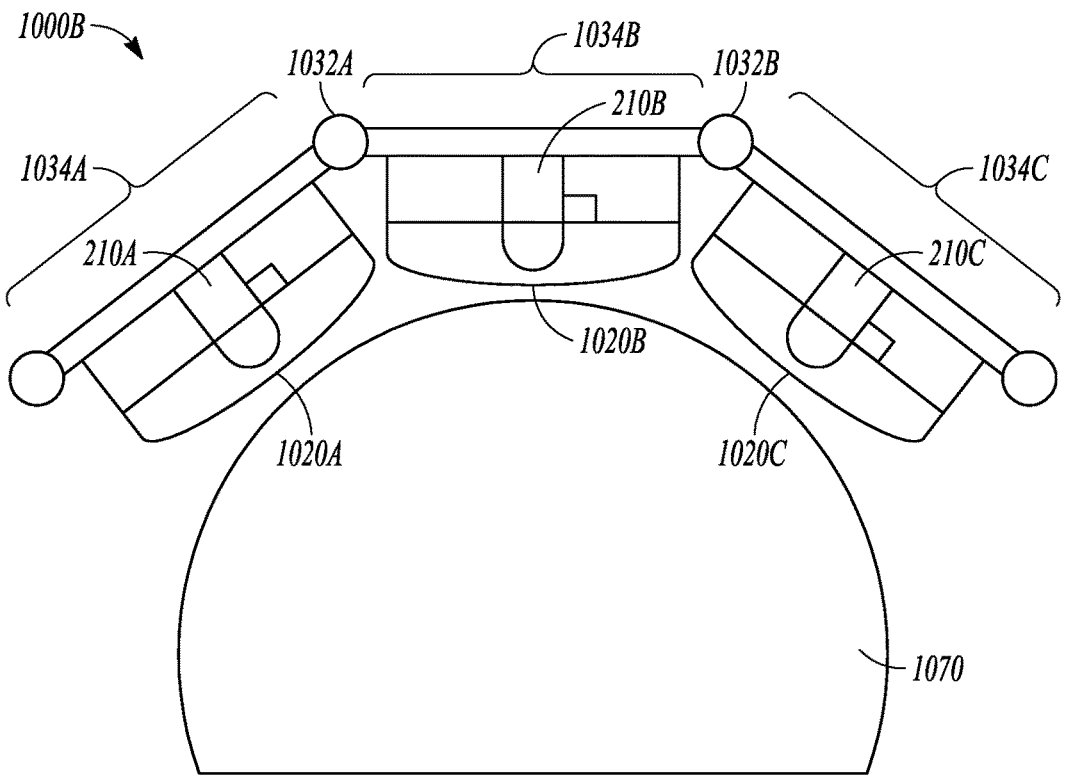

FIGS. 10A and 10B illustrate generally portions of other illustrative examples of a hand-held ultrasonic transducer assembly, such as including a mechanical coupling between respective portions of a housing. The configuration shown in FIGS. 10A and 10B can include an articulated configuration such as conformable to a tissue site 1070. One or more transducer elements can be arranged to couple ultrasonic energy to a target via a deformable coupling pad. However, in addition to using a deformable coupling pad, or instead of using a deformable coupling pad, one or more transducers can be conformed to a tissue surface (e.g., a leg) such as by placing transducer elements on respective frame units (or other mountings) that can adjust or to conform portions of the assembly to the tissue surface. Such an articulated arrangement can include one or more hinges. Such a hinge or other articulated coupling can include an encoder, such as one or more angle encoders. Such an encoder can provide information about a transducer angle or position with respect to one or more other transducers, or with respect to one or more fiducial positions, for use in processing echo information or image reconstruction.

For example, in FIG. 10A, a first housing portion 1030A can be coupled to a first ultrasonic transducer 210A, and to an articulated mechanical coupling 1032, such as a hinge or rotatable joint. A second housing portion 1030B can be coupled to a second ultrasonic transducer 210B, and to the articulated mechanical coupling 1032. In this manner, the two transducers 210A and 210B, or one or more other transducers, can be user-positioned to conform to a tissue site, and to acquire overlapping scan planes or scan volumes. Similarly, additional articulated mechanical couplings can be provided, such as a second articulated mechanical coupling 1032B, coupled to a third transducer 210C. In this manner, as shown in FIG. 10B, a first transducer assembly 1034A, a second transducer assembly 1034B, and a third transducer assembly 1034C can be positioned with respect to one another around the tissue site 1070. The use of three assemblies 1034A through 1034C in FIG. 10C is illustrative, and more assemblies can be similarly coupled together using articulated or fixed couplings. In the examples of FIGS. 10A and 10B, a first coupling pad 1020A, a second coupling pad 1020B, or a third coupling pad 1020C (as in FIG. 10B) can be used. Such coupling pads can be rigid or deformable.

Figure 11:
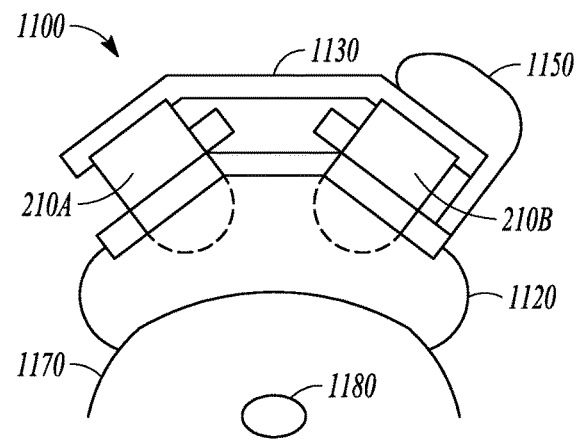
FIG. 11 illustrates generally yet another illustrative example of a hand-held ultrasonic transducer assembly, such as including two or more transducers in fixed locations with respect to each other.

FIG. 11 illustrates generally yet another illustrative example of a hand-held ultrasonic transducer assembly 1100, such as including two or more transducers in fixed locations with respect to each other. Similar to the fixed-angle example discussed in relation to FIG. 5, the assembly 1100 shown in FIG. 11 can include a first ultrasonic transducer 210A and a second ultrasonic transducer 210B, such as anchored at respective fixed locations and angles with respect to each other within a housing 1130 or along a rail or other mechanical coupling. A coupling pad 1120, which can be rigid or deformable, can be used to acoustically couple energy to and from the first and second ultrasonic transducers 210A or 210B. In this manner, spatially overlapping scan planes or volumes can be acquired, such as to reconstruct an image of a bone 1180 or other imaging target. To help a user manipulate the assembly 1100, a grip 1150 or handle can be included, such as a rigid or padded grip.

Figures 12A, 12B:
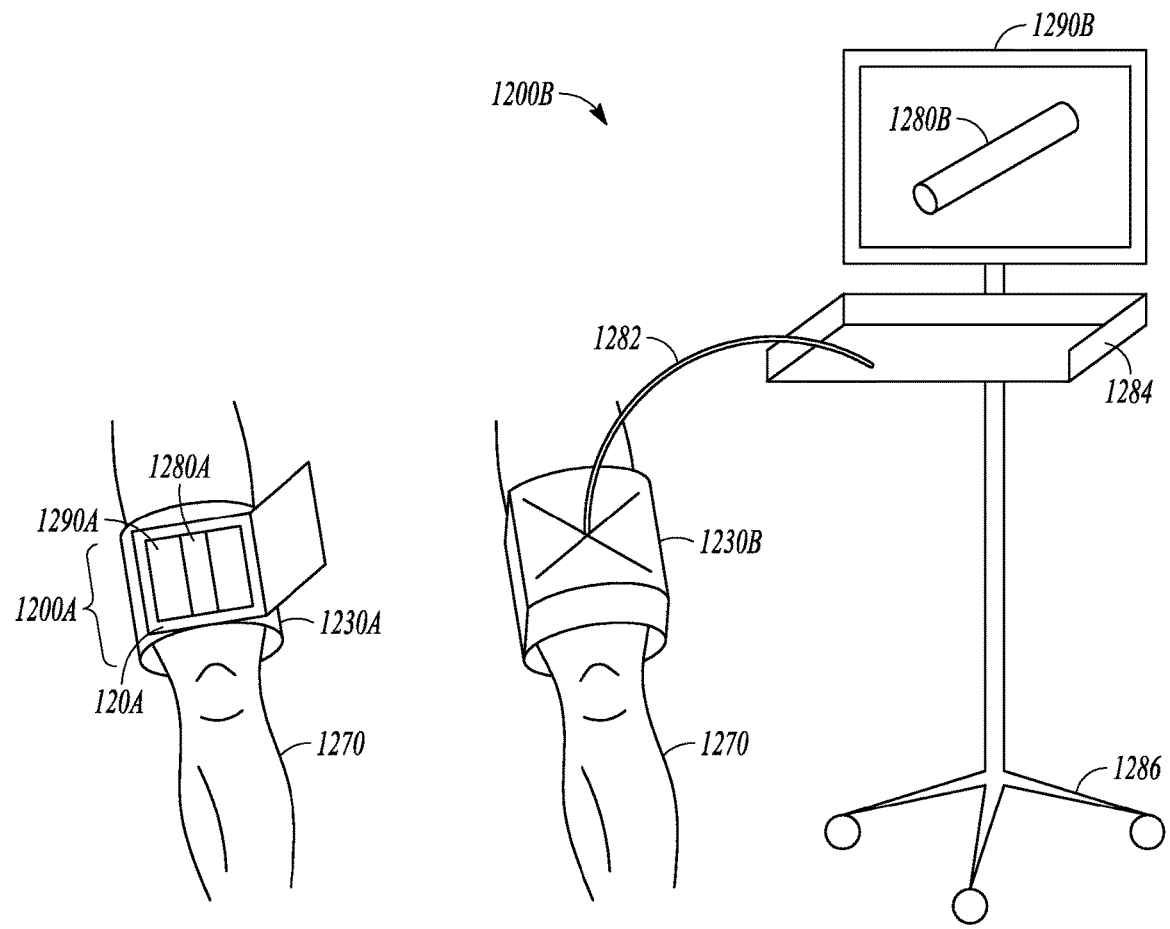
FIGS. 12A and 12B illustrate generally other illustrative examples of ultrasonic transducer assemblies, such as can include a hand-held assembly including a display (e.g., in FIG. 12A) or a transducer assembly coupled to a separate display (e.g., in FIG. 12B).

FIGS. 12A and 12B illustrate generally other illustrative examples of ultrasonic transducer assemblies, such as can include a user-manipulatable or hand-held assembly 1200A including a display (e.g., in FIG. 12A) or a system 1220B including a transducer assembly 1230B coupled to a separate display 1280B (e.g., in FIG. 12B). In the example of FIG. 12A, a display 1290A can present a reconstructed image of an imaging target 1280A, such as bone, using echo information obtained from one or more ultrasonic transducers included as a portion of the assembly 1200A. The imaging display can be presented in a spatially-registered manner with respect to underlying tissue, such as with respect to bone anatomy within a leg 1270. In the example of FIG. 12B, the transducer assembly 1230B can obtain echo information, and such information can be coupled through a wired link 1282 or wirelessly to a separate location, such as a nearby station or cart 1286. Such a station or cart 1286 can include a processor circuit or other hardware, such as in a region 1284, for processing the obtained echo information in order to present an image of an imaging target 1280B on the display 1290B.

Figure 13A:
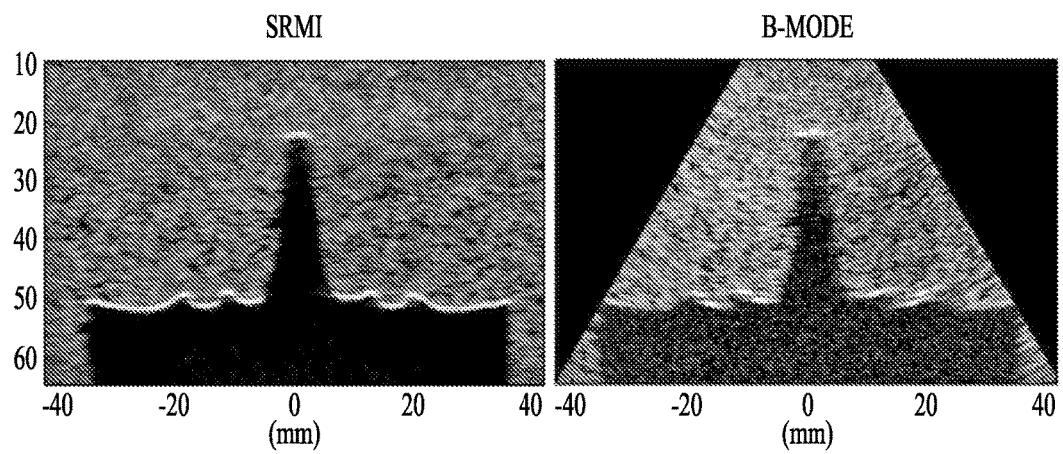
FIGS. 13A through 13C illustrate generally various illustrative examples including simulated ultrasound images in FIG. 13 A, and experimentally-obtained images processed using various techniques in FIG. 13B, and a three-dimensional image rendered from a compilation of experimentally-obtained two-dimensional images in FIG. 13C.
Figure 13B:
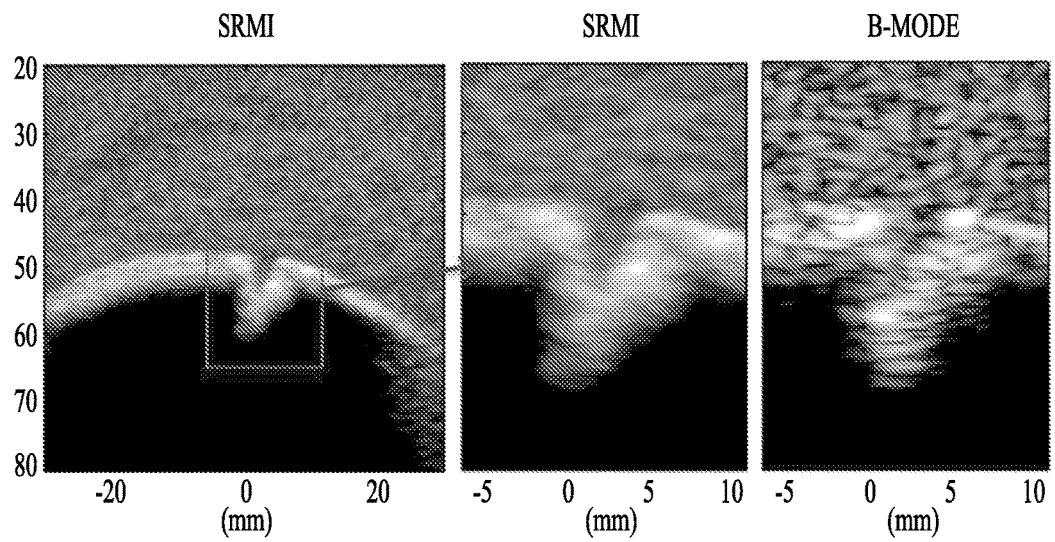
Figure 13C:
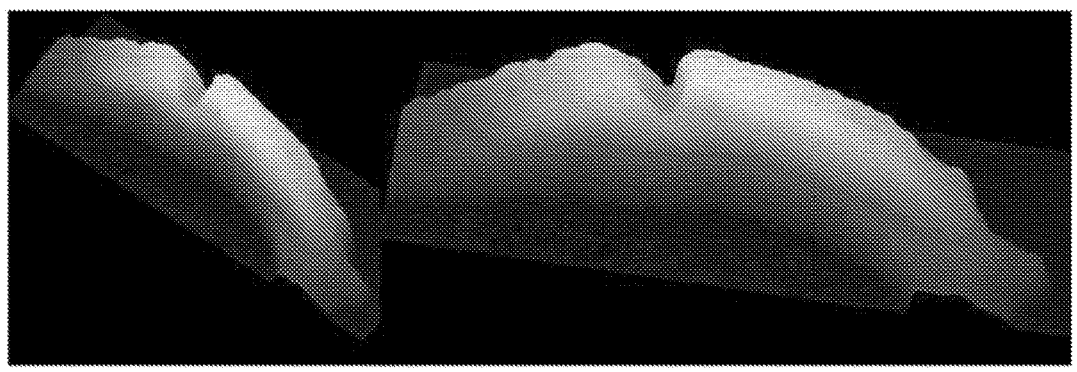

FIGS. 13A through 13C illustrate generally various illustrative examples including simulated ultrasound images in FIG. 13 A, experimentally-obtained images processed using various techniques in FIG. 13B, and a three-dimensional image rendered from a compilation of experimentally-obtained two-dimensional images in FIG. 13C. In FIG. 13A, a simulated ultrasound image is shown including processing using an SRMI approach as compared to a generally-available B-mode imaging techniques, rendered using FIELD II software. Experimentally-obtained images are shown in FIG. 13B, including images of an excised porcine rib fracture embedded in a tissue-mimicking gelatin. Such experimentally-obtained images are rendered using an SRMI technique in FIG. 13B, including an inset, and the SRMI-processed images demonstrate enhanced bone delineation as compared with a B-mode image rendered using generally-available B-mode imaging techniques. A compilation of 2D images can be used for generation of a 3D representation, using an SRMI technique, as shown in FIG. 13C.

Generally, the SRMI technique can be used to render (e.g., construct) images, such as from one or more of a characteristic of the reflection magnitude or phase profile across multiple angles of interrogation. For example, rather than superimposing overlapping image scans, a profile for respective points can be created where respective constituents of such a profile can represent information obtained using respective, different, angles of interrogation (e.g., a reflection amplitude or other characteristic corresponding to respective different transducer locations). Properties from such a profile can be extracted, such as a slope or a surface normal. Such properties can be rendered for display to a user, using an SRMI technique.

Angular profile properties can be used to classify tissue types into specular versus diffusive targets, for example. In one approach, an angular scatter imaging technique can be used, such as described in Walker W F; *C and D-weighted ultrasonic imaging using the translating apertures algorithm*, IEEE Transactions on Ultrasonics Ferroelectrics and Frequency Control; 2001; 48(2):452-61. Because a profile for respective points in a reconstructed image can be determined using information obtained from different transducer interrogations at different angles, respective points can be associated with respective vectors. Such vectors can be used in one or more of linear or non-linear techniques, such as to discriminate bone (or one or more other substantially specular targets) from other non-specular targets or a background non-specular (e.g., speckle) acoustic signature, such as to identify specular-reflecting target properties.

In one approach, a non-linear discrimination technique can include a singular value filter technique. In one approach, a linear discrimination technique can be used, such as to identify bone properties. For example, a location can be identified as bone, such as due to extremely bright reflections using an SRMI technique. The information vector at such a location can include reflections from several transducers at different angles. A surface normal direction can be extracted, using, for example, an interrogation angle providing a brighter or brightest reflection, or including curve fitting from specular reflector angular reflectivity over several angles. A surface normal direction of bone generally varies slowly, and can vary with spatial motion. Such variation can be provide further information to identify and discriminate bone surfaces from other reflectors or media.

Considerations related to bone imaging and localization are also discussed in Mauldin F W, Jr, Owen K, Tiouririne M, Hossack J A; *The effects of transducer geometry on artifacts common to diagnostic bone imaging with conventional medical ultrasound*, IEEE Transactions on Ultrasonics, Ferroelectrics, and Frequency Controls; June 2012; 59(6):1101-14, and Hacihaliloglu I, Abugharbieh R, Hodgson A J, Rohling R N; *Bone surface localization in ultrasound using image phase-based feature*; Ultrasound in Medicine and Biology; 2009; 35(9):1475-87.

SRMI reconstruction techniques can be superior to generally-available techniques in delineation of tissue interfaces (e.g., such as including an interface between soft tissue and bone). An SRMI technique can include superimposing overlapping regions of envelope-detected ultrasound echo information, such as acquired from transducers positioned at different locations. Generally, acoustic energy reflected from a specular surface (e.g., bone) back to the transducer face decreases as an angle of incidence deviates from 90 degrees. For this reason, among others, interrogation (e.g., obtaining ultrasound energy reflected from a target) at a single or narrow range of angles of incidence can result in reconstructed images that lack bright reflections at bone surface locations, because of such bone surfaces can have a non-perpendicular angle to the beam (such as shown in the B-mode example of FIG. 13A).

Because scans (e.g., sector plane or volume scans) from different transducers overlap using an SRMI technique, bone surfaces are interrogated at more than one angle (e.g., many different angles). For example, respective sector scans can provide enhanced sensitivity to different angular surface components of the bone structure of interest (e.g., as shown in the SRMI examples of FIG. 13B). Such techniques can enhance signal-to-noise ratio (SNR). Speckle (e.g., an ultrasound image pattern generated from diffusive scatterers, such as soft tissue) can be compounded, such as made more homogeneous or showing reduced variation therein, such as using an SRMI technique, which can further enhance bone delineation on a displayed representation of the region being interrogated.

Figure 14A:
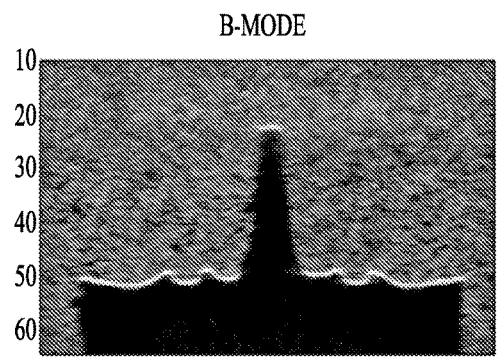
FIGS. 14A through 14E illustrate generally a comparison between simulated ultrasound images obtained using a generally-available B-mode imaging technique in FIG. 14A, versus using a Specular surface Reconstruction from Multi-angle Interrogation (SRMI) technique and various transducers spacings as shown in the examples of FIGS. 14B through 14E.
Figure 14B:
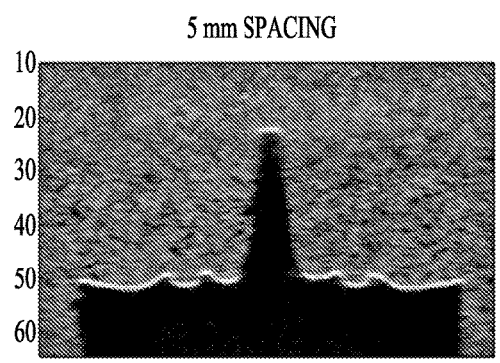
Figure 14C:
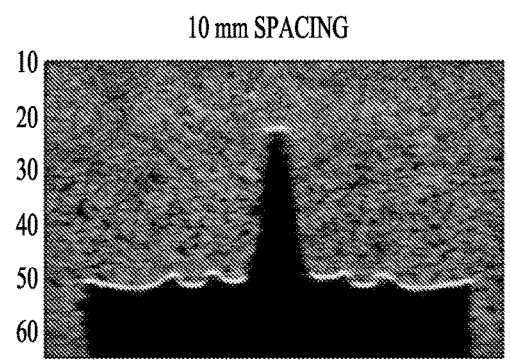
Figure 14D:
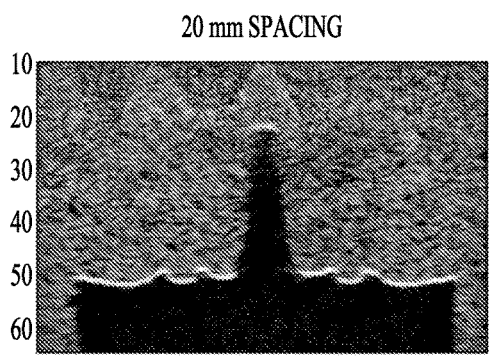
Figure 14E:
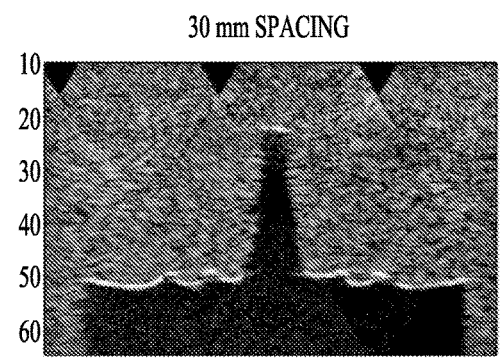

FIGS. 14A through 14E illustrate generally a comparison between simulated 2D ultrasound images obtained using a generally-available B-mode imaging technique in FIG. 14A, versus using an SRMI technique and various transducers spacing as shown in the examples of FIGS. 14B through 14E, simulated using FIELD II software. In the illustrative example of FIGS. 14A through 14E, transducers can be "wobbled" such as to provide a 60-degree sector scan. Sector scans can be overlapping, for example, such that bone surfaces are interrogated from multiple angles. Envelope-detected images from respective transducers or transducer positions can be superimposed to form an SRMI image representation, for a 5 millimeter (mm) spacing as shown in FIG. 14B, a 10 mm spacing as shown in FIG. 14C, a 20 mm spacing as shown in FIG. 14D, and a 30 mm spacing as shown in FIG. 14E.

Figure 15:
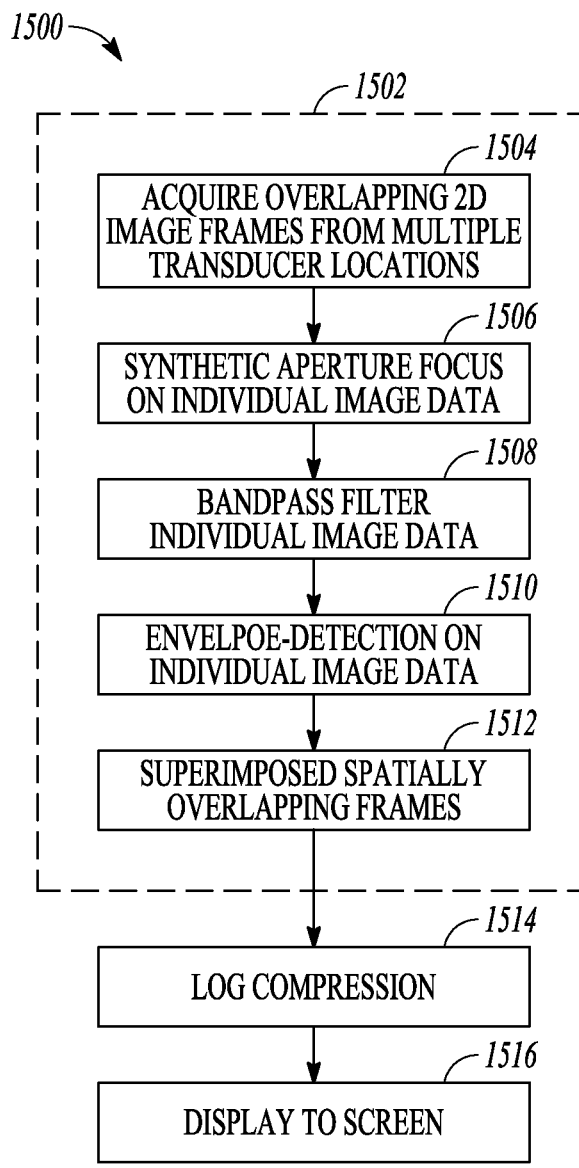
FIG. 15 illustrates generally a technique, such as a method, that can include a Specular surface Reconstruction using Multi-angle Interrogation (SRMI) technique.

FIG. 15 illustrates generally a technique 1500, such as a method, that can include a Specular surface Reconstruction using Multi-angle Interrogation (SRMI) technique 1502. At 1504, spatially overlapping image frames (e.g., sector scan planes or volumes) can be acquired corresponding to multiple transducer locations. At 1506, a synthetic aperture focusing technique can be performed on individual image data (e.g. on respective frames). In an example, such synthetic aperture focusing need not be performed.

At 1508 the individual image data can be bandpass filtered, or filtered using other techniques. At 1510, individual image data can be envelope-detected, and at 1512 spatially-overlapping frames can be superimposed on each other. At 1514, a log compression can be applied to the superimposed spatially-overlapping frames, and such information can be stored or, at 1516, displayed.

Figure 16:
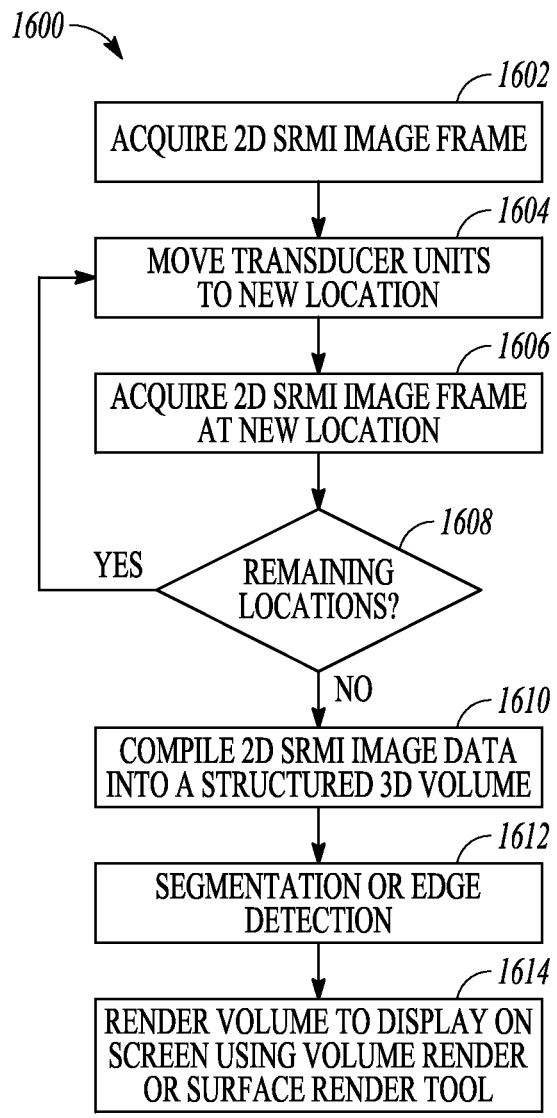
FIG. 16 illustrates generally, a technique, such as a method, that can include using a Specular surface Reconstruction from Multi-angle Interrogation (SRMI) technique to generate a three-dimensional representation of obtained ultrasound echo information.

FIG. 16 illustrates generally, a technique, such as a method, that can include using a Specular surface Reconstruction from Multi-angle Interrogation (SRMI) technique to generate a three-dimensional (3D) representation of obtained ultrasound echo information. At 1602, an image frame can be acquired, such as an image frame reconstructed at the output of a 2D SRMI technique, as provided using the SRMI technique 1502 of FIG. 15. For example, a 2D SRMI image frame can itself be constructed using echo information obtained from spatially overlapping scan planes as discussed in other examples, to provide an image frame including superimposed information obtained from the overlapping scan planes.

At 1604, a mechanically-scanned transducer or a transducer array can be moved to a new location, and another 2D SRMI image frame can be acquired. At 1608, if additional locations remain to be scanned, the technique 1600, and including moving the transducer units to another new location at 1604 and acquiring another 2D SRMI image frame at 1606.

At 1610, the 2D SRMI image data (e.g., the 2D SRMI image frames) can be compiled into a structured 3D volume. At 1612, segmentation or edge detection can be performed, and at 1614, the volume can be rendered for display using a volume or surface rendering technique. Various segmentation, volume, or surface rendering techniques can be used to construct an image for display to user, such as including information obtained using an SRMI technique, such as to provide a 2D or 3D representation of a target for display to a user. For example, open-source software toolkits can be used for such rendering techniques, including one or more of Insight Toolkit (ITK), or Visualization Toolkit (VTK), both available from Kitware (Clifton Park, N.Y.).

Figure 17A:
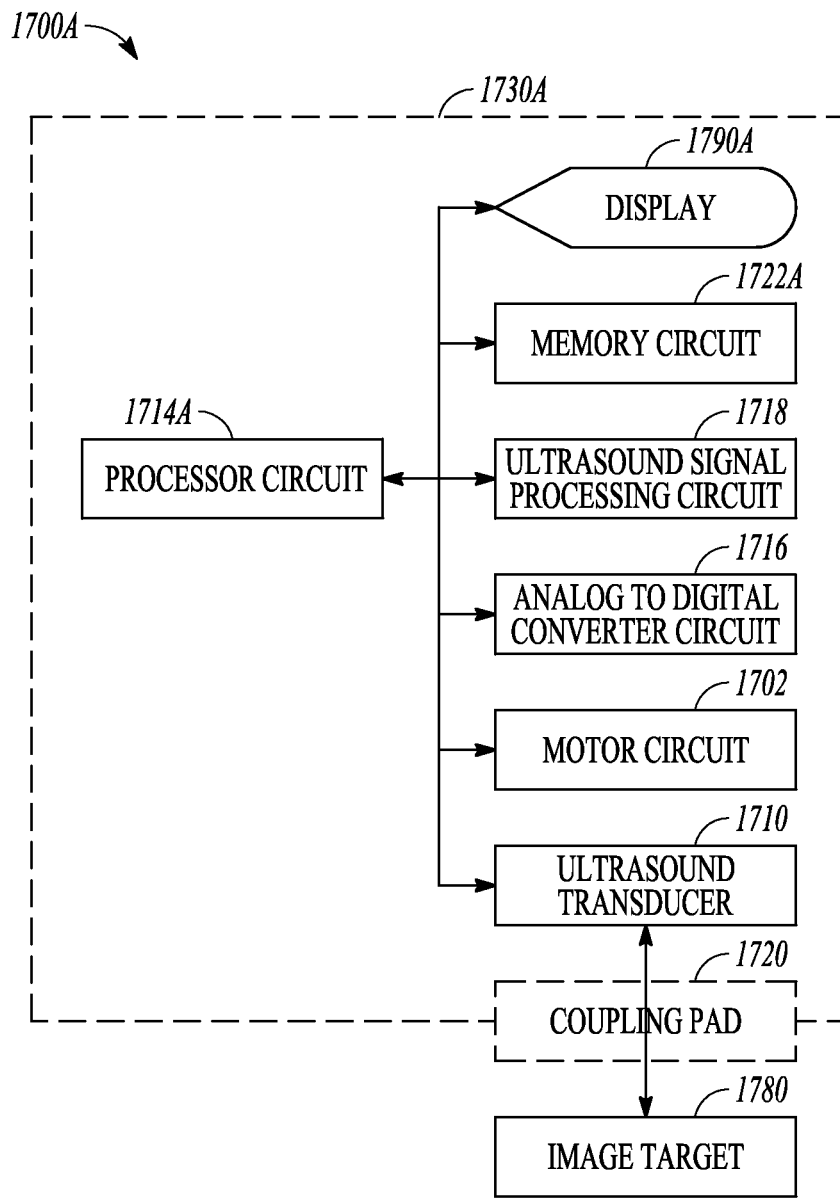
FIG. 17A illustrates generally an apparatus that can include a display, one or more processor circuits, one or more other circuits such as a memory circuit, an ultrasound signal processor circuit, an analog-to-digital converter circuit, a motor circuit, or one or more ultrasonic transducers.

FIG. 17A illustrates generally an apparatus 1700A that can include a display 1790A, one or more processor circuits 1724A, one or more other circuits such as a memory circuit 1722A, an ultrasound signal processing circuit 1718, an analog-to-digital converter circuit 1716, a motor circuit 1702, or one or more ultrasonic transducers, such as an ultrasound transducer 1710. As discussed in the examples above, a coupling pad 1720 can be included, such as to conformably or rigidly couple ultrasound energy between an imaging target 1780, such as located within a tissue volume, and the ultrasound transducer 1710. The apparatus of FIG. 17A can include a self-contained 3D imaging apparatus, such as including a hand-held or user-manipulated apparatus as shown and described in other examples herein (e.g., FIG. 4A or 4B, FIG. 9C, FIG. 11, or FIG. 12A).

Figure 17B:
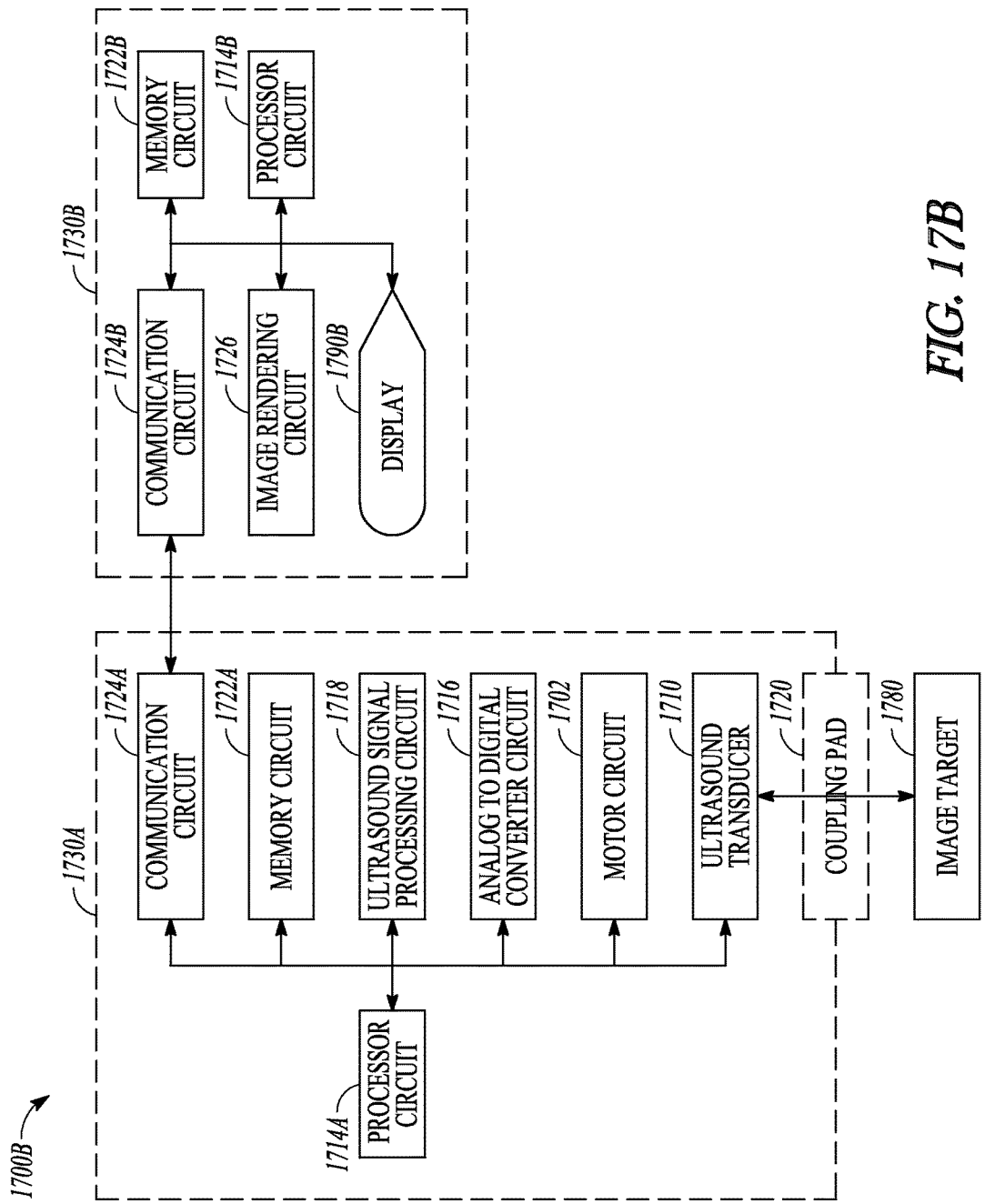
FIG. 17B illustrates generally an apparatus that can include a display, one or more processor circuits, one or more other circuits such as a memory circuit, an ultrasound signal processor circuit, an analog-to-digital converter circuit, a motor circuit, or one or more ultrasonic transducers, such as can include a transducer unit housing and a display unit housing.

FIG. 17B illustrates generally an apparatus that can include a display 1790B, one or more processor circuits, one or more other circuits such as a memory circuit, an ultrasound signal processor circuit, an analog-to-digital converter circuit, a motor circuit, or one or more ultrasonic transducers, such as can include a transducer assembly housing 1730A and a display assembly housing 1730B.

For example, one or more of obtaining ultrasonic echo information or other techniques can be performed such as using circuitry included as a portion of the transducer assembly housing 1730A, such as using one or more of a first processor circuit 1724A, a first memory circuit 1722A, an ultrasound signal processing circuit 1718, an analog-to-digital converter circuit 1716, or a motor circuit 1702. A communication circuit 1724A can provide a wired or wireless link, such as can include a WiFi or Bluetooth link that can be used to transmit imaging information, or another representation of received ultrasonic echo information, such as for display at the location of the display assembly housing 1730B. The display assembly housing 1730B can include a second processor circuit 1724B, a second memory circuit 1722B, an image rendering circuit 1726, and a display. In this manner, the transducer assembly housing 1730 can be separately manipulated by a user, and a displayed reconstruction of an imaging target 1780 can be observed at a remotely located or nearby station where the display assembly housing 1730B and display 1790B are located.

In various examples herein, including one or more of the apparatus 1700A or the apparatus 1700B, an ultrasound apparatus can be used to obtain echo information from one or more ultrasonic transducers, and to construct or present an constructed image to a user, such as including an image of an at least partially specular-reflecting target such as bone. In an example, such ultrasound apparatus can include a single element array, a conformable transducer surface, and can include using an SRMI image reconstruction techniques. Such apparatus can provide advantages over generally-available 2D ultrasound apparatus or techniques, such as to provide: 1) reduced image artifact, 2) increased field of view, or 3) conformability to the shape of the patient's skin surface.

In particular, an array of piston transducers will not exhibit grating-lobe-derived artifacts, and can yield superior bone image contrast. An increased field of view can be advantageous compared with generally-available ultrasound apparatus or techniques because such a field of view can significantly reduce a burden on the user in acquiring or interpreting resulting images. Such burden can also be reduced such as by generating or presenting a 3D representation of a target. In an example, an ultrasound operator can manipulate a small transducer to an orientation to observe a preferred scan plane. To visualize 3D structures, such an operator can translate the device across the skin while "building up" a mental 3D image of tissue structures or by compiling successive 2D representations into a rendered 3D representation.

VARIOUS NOTES & EXAMPLES

Example 1 can include or use subject matter (such as an apparatus, a method, a means for performing acts, or a device readable medium including instructions that, when performed by the device, can cause the device to perform acts), such as can include or use an ultrasound diagnostic apparatus, comprising one or more ultrasonic transducers configured to mechanically scan a tissue region including an imaging target, and a mechanical positioner configured to position the one or more ultrasonic transducers to receive first echo information corresponding to a first volume of tissue defined at least in part by a first location of one or more ultrasonic transducers and receive second echo information corresponding to a second volume of tissue defined at least in part by a second location of one or more ultrasonic transducers, the second volume spatially overlapping with the first volume of tissue in a portion of the tissue region. In Example 1, the first location and the second location are separated by at least about one wavelength corresponding to a center frequency of ultrasonic energy used for tissue insonification.

Example 2 can include, or can optionally be combined with the subject matter of Example 1, to optionally include one or more ultrasonic transducers comprising a piston transducer.

Example 3 can include, or can optionally be combined with the subject matter of one or any combination of Examples 1 or 2 to optionally include obtaining echo information from an imaging target including an at least approximately specular-reflecting target.

Example 4 can include, or can optionally be combined with the subject matter of one or any combination of Examples 1 through 3 to optionally include one or more ultrasonic transducers comprising an array of transducers having a separation between adjacent transducers of at least about a wavelength corresponding to a center frequency of ultrasonic energy for tissue insonification.

Example 5 can include, or can optionally be combined with the subject matter of one or any combination of Examples 1 through 4 to optionally include a mechanical positioner comprising a motorized mechanical actuator.

Example 6 can include, or can optionally be combined with the subject matter of Example 5, to optionally include a mechanical actuator configured to one or more of rotate and translate the one or more ultrasonic transducers.

Example 7 can include, or can optionally be combined with the subject matter of one or any combination of Examples 1 through 6 to optionally include a mechanical positioner comprising a user-adjustable portion to establish a location of a first ultrasonic transducer in the first location and a second ultrasonic transducer in the second location.

Example 8 can include, or can optionally be combined with the subject matter of Example 7, to optionally include a housing, and a mechanical positioner comprising a hand-adjustable articulating mechanical coupling coupled to the housing.

Example 9 can include, or can optionally be combined with the subject matter of Example 8, to optionally include a first portion of the housing comprising the first ultrasonic transducer and a second portion of the housing comprising the second ultrasonic transducer.

Example 10 can include, or can optionally be combined with the subject matter of one or any combination of Examples 1 through 4 to optionally include a coupling pad configured to conform to a surface shape of a surface of the tissue region and configured to acoustically couple the one or more ultrasonic transducers to the tissue region.

Example 11 can include, or can optionally be combined with the subject matter of one or any combination of Examples 1 through 10 to optionally include a coupling pad that is deformable.

Example 12 can include, or can optionally be combined with the subject matter of one or any combination of Examples 10 or 11 to optionally include s coupling pad defining a cavity including a coupling fluid, where the one or more ultrasonic transducers are acoustically coupled to the surface of the tissue region via the coupling fluid.

Example 13 can include, or can optionally be combined with the subject matter of one or any combination of Examples 1 through 12 to optionally include a processor circuit, configured to obtain echo information from the one or more ultrasonic transducers, the processor circuit programmed to obtain the first echo information corresponding to the first volume of tissue, obtain the second echo information corresponding to the second volume of tissue, construct at least one of a two dimensional (2D) or a three dimensional (3D) representation of the imaging target using the obtained first and second echo information.

Example 14 can include, or can optionally be combined with the subject matter of Example 13 to optionally include a display, where the processor circuit is programmed to display at least one of the 2D or 3D representation of the imaging target.

Example 15 can include, or can optionally be combined with the subject matter of Example 14 to optionally include a housing, where the housing includes the one or more ultrasonic transducers and the display.

Example 16 can include, or can optionally be combined with the subject matter of one or any combination of Examples 1 through 15 to include, subject matter (such as an apparatus, a method, a means for performing acts, or a machine readable medium including instructions that, when performed by the machine, that can cause the machine to perform acts), such as can include receiving first echo information from one or more ultrasonic transducers corresponding to a first volume of tissue defined at least in part by a first location of the one or more ultrasonic transducers, receiving second echo information from one or more ultrasonic transducers corresponding to a second volume of tissue defined at least in part by a second location of the one or more ultrasonic transducers, the second volume spatially overlapping with the first volume of tissue in a tissue region being scanned, and constructing at least one of a two dimensional (2D) or a three dimensional (3D) representation of the imaging target using the obtained first and second echo information, where the first location and the second location are separated by at least about one wavelength corresponding to a center frequency of ultrasonic energy used for tissue insonification.

Example 17 can include or use subject matter (such as an apparatus, a method, a means for performing acts, or a device readable medium including instructions that, when performed by the device, can cause the device to perform acts), such as can include or use an ultrasonic diagnostic apparatus, comprising at least two ultrasonic transducers configured to insonify a tissue region including an at least approximately specular-reflecting target, a coupling pad configured to conform to a surface shape of a surface of the tissue region and configured to acoustically couple the at least two ultrasonic transducers to the tissue region, and a processor circuit, configured to obtain echo information from the one or more ultrasonic transducers, the processor circuit programmed to obtain first echo information corresponding to a first volume of tissue defined at least in part by an ultrasonic transducer at a first location and obtain second echo information corresponding to a second volume of tissue defined at least in part by an ultrasonic transducer at a second location, the second volume spatially overlapping with the first volume of tissue.

Example 18 can include, or can optionally be combined with the subject matter of Example 17, to optionally include a coupling pad that is deformable.

Example 19 can include, or can optionally be combined with the subject matter of Example 18, to optionally include a coupling pad defining a cavity including a coupling fluid, where the at least two transducers are acoustically coupled to the surface of the tissue region via the coupling fluid.

Example 20 can include, or can optionally be combined with any portion or combination of any portions of any one or more of Examples 1 through 19 to include, subject matter that can include means for performing any one or more of the functions of Examples 1 through 19, or a machine-readable medium including instructions that, when performed by a machine, cause the machine to perform any one or more of the functions of Examples 1 through 19. Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with The claimed invention is:

1. An ultrasound diagnostic apparatus, comprising:
    one or more ultrasonic transducers configured to mechanically scan a tissue region including an imaging target; and
    a mechanical positioner configured to position the one or more ultrasonic transducers to:
    receive first echo information corresponding to a first volume of tissue defined at least in part by a first location of one or more ultrasonic transducers; and
    receive second echo information corresponding to a second volume of tissue defined at least in part by a second location of one or more ultrasonic transducers, the second volume spatially overlapping with the first volume of tissue in a portion of the tissue region;
    wherein the first location and the second location are separated by at least one wavelength corresponding to a center frequency of ultrasonic energy used for tissue insonification.

2. The ultrasound diagnostic apparatus of claim 1, wherein the one or more ultrasonic transducers include a piston transducer.

3. The ultrasound diagnostic apparatus of claim 1, wherein the imaging target comprises at least a specular-reflecting target.

4. The ultrasonic diagnostic apparatus of claim 1, wherein the one or more ultrasonic transducers include an array of transducers having a separation between adjacent transducers of at least a wavelength corresponding to a center frequency of ultrasonic energy for tissue insonification.

5. The ultrasound diagnostic apparatus of claim 1, wherein the mechanical positioner includes a motorized mechanical actuator.

6. The ultrasound diagnostic apparatus of claim 5, wherein the mechanical actuator is configured to one or more of rotate and translate the one or more ultrasonic transducers.

7. The ultrasound diagnostic apparatus of claim 1, wherein the mechanical positioner includes a user-adjustable portion to establish a location of a first ultrasonic transducer in the first location and a second ultrasonic transducer in the second location.

8. The ultrasound diagnostic apparatus of claim 7, comprising a housing; and
    wherein the mechanical positioner includes a hand-adjustable articulating mechanical coupling coupled to the housing.

9. The ultrasonic diagnostic apparatus of claim 8, wherein a first portion of the housing includes the first ultrasonic transducer; and
    wherein a second portion of the housing includes the second ultrasonic transducer.

10. The ultrasound diagnostic apparatus of claim 1, comprising a coupling pad configured to conform to a surface shape of a surface of the tissue region and configured to acoustically couple the one or more ultrasonic transducers to the tissue region.

11. The ultrasonic diagnostic apparatus of claim 10, wherein the coupling pad is deformable.

12. The ultrasonic diagnostic apparatus of claim 10, wherein the coupling pad defines a cavity including a coupling fluid; and
    wherein the one or more ultrasonic transducers are acoustically coupled to the surface of the tissue region via the coupling fluid.

13. The ultrasound diagnostic apparatus of claim 1, comprising a processor circuit, configured to obtain echo information from the one or more ultrasonic transducers, the processor circuit programmed to:
    obtain the first echo information corresponding to the first volume of tissue;
    obtain the second echo information corresponding to the second volume of tissue; and
    construct at least one of a two dimensional (2D) or a three dimensional (3D) representation of the imaging target using the obtained first and second echo information.

14. The ultrasonic diagnostic apparatus of claim 13, comprising a display;
    wherein the processor circuit is programmed to display at least one of the 2D or 3D representation of the imaging target.

15. The ultrasonic diagnostic apparatus of claim 14, comprising a housing;
    wherein the housing includes the one or more ultrasonic transducers and the display.

16. An ultrasonic imaging method, comprising receiving first echo information from one or more ultrasonic transducers corresponding to a first volume of tissue defined at least in part by a first location of the one or more ultrasonic transducers;
    receiving second echo information from one or more ultrasonic transducers corresponding to a second volume of tissue defined at least in part by a second location of the one or more ultrasonic transducers, the second volume spatially overlapping with the first volume of tissue in a tissue region being scanned; and
    constructing at least one of a two dimensional (2D) or a three dimensional (3D) representation of the imaging target using the obtained first and second echo information; wherein the first location and the second location are separated by at least one wavelength corresponding to a center frequency of ultrasonic energy used for tissue insonification.

17. A processor-readable medium comprising instructions that, when performed by one or more processors, cause an apparatus to perform an ultrasound imaging method as recited in claim 16.

18. An ultrasonic diagnostic apparatus, comprising:
    at least two ultrasonic transducers configured to insonify a tissue region including at least a specular-reflecting target;
    a coupling pad configured to conform to a surface shape of a surface of the tissue region and configured to acoustically couple the at least two ultrasonic transducers to the tissue region; and
    a processor circuit, configured to obtain echo information from the one or more ultrasonic transducers, the processor circuit programmed to:
    obtain first echo information corresponding to a first volume of tissue defined at least in part by an ultrasonic transducer at a first location; and
    obtain second echo information corresponding to a second volume of tissue defined at least in part by an ultrasonic transducer at a second location, the second volume spatially overlapping with the first volume of tissue;
    wherein the first location and the second location are separated by at least one wavelength corresponding to a center frequency of ultrasonic energy used for tissue insonification.

19. The ultrasonic diagnostic apparatus of claim 18, wherein the coupling pad is deformable.

20. The ultrasonic diagnostic apparatus of claim 19, wherein the coupling pad defines a cavity including a coupling fluid; and
 wherein the at least two transducers are acoustically coupled to the surface of the tissue region via the coupling fluid.

\* \* \* \* \*